(12) United States Patent
Wikswo et al.

(10) Patent No.: US 10,538,726 B2
(45) Date of Patent: Jan. 21, 2020

(54) SYSTEM AND METHOD FOR MICRODIALYSIS IMAGING AND REGIONAL FLUIDIC DELIVERY AND CONTROL AND APPLICATIONS OF SAME

(71) Applicant: VANDERBILT UNIVERSITY, Nashville, TN (US)

(72) Inventors: John P. Wikswo, Brentwood, TN (US); Ronald S. Reiserer, Nashville, TN (US); Kyle Hawkins, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 16/397,019

(22) Filed: Apr. 29, 2019

(65) Prior Publication Data

US 2019/0249128 A1 Aug. 15, 2019

Related U.S. Application Data

(60) Continuation-in-part of application No. 16/012,900, filed on Jun. 20, 2018, which is a division of
(Continued)

(51) Int. Cl.
*C12M 3/06* (2006.01)
*C12M 1/36* (2006.01)
(Continued)

(52) U.S. Cl.
CPC .......... *C12M 23/16* (2013.01); *A01N 1/0247* (2013.01); *B01L 3/5027* (2013.01); *C12M 23/12* (2013.01);
(Continued)

(58) Field of Classification Search
CPC ...... C12M 23/16; C12M 23/58; C12M 23/12; C12M 23/44; C12M 25/02; C12M 29/00;
(Continued)

(56) References Cited

U.S. PATENT DOCUMENTS

| 9,618,129 B2 | 4/2017 | Block, III et al. |
| 2013/0027695 A1* | 1/2013 | Salsman ............. B01L 3/50273 356/246 |

OTHER PUBLICATIONS

Caldwell, R. L. and R. M. Caprioli (2005). "Tissue profiling by mass spectrometry—A review of methodology and applications." Molecular and Cellular Proteomics 4(4): 394-401.
(Continued)

*Primary Examiner* — Michael L Hobbs
(74) *Attorney, Agent, or Firm* — Locke Lord LLP; Tim Tingkang Xia, Esq.

(57) ABSTRACT

A system for microdialysis imaging and regional fluidic delivery and control includes a microdialysis imager including a imaging head having N pixels aligned in a pixel array for monitoring a living bio-object associated with the pixel array; and a fluidic module coupled to the microdialysis imager for delivering a fluidic substance to and collecting effluent from the living bio-object, including a fluidic network having a plurality of valves, a plurality of fluidic channels in fluidic communication with the plurality of valves and one or more pumps coupled to corresponding fluidic channels, and a microcontroller coupled to the fluidic network for individually controlling the plurality of valves and the one or more pumps of the fluidic network as so to operably and selectively deliver the fluidic substance to and continuously collect the effluent from the living bio-object responsive to the delivered fluidic substance via each pixel in real time.

35 Claims, 14 Drawing Sheets

Related U.S. Application Data application No. 15/191,092, filed on Jun. 23, 2016, now Pat. No. 10,023,832, and a continuation-in-part of application No. 13/877,925, filed as application No. PCT/US2011/055432 on Oct. 7, 2011, now abandoned, said application No. 15/191,092 is a continuation-in-part of application No. 14/363,074, filed as application No. PCT/US2012/068771 on Dec. 10, 2012, now Pat. No. 10,078,075, said application No. 15/191,092 is a continuation-in-part of application No. 14/646,300, filed as application No. PCT/US2013/071026 on Nov. 20, 2013, now Pat. No. 9,874,285, said application No. 15/191,092 is a continuation-in-part of application No. 14/651,174, filed as application No. PCT/US2013/071324 on Nov. 21, 2013, now Pat. No. 9,618,129.

(60) Provisional application No. 62/664,499, filed on Apr. 30, 2018, provisional application No. 62/183,571, filed on Jun. 23, 2015, provisional application No. 62/193,029, filed on Jul. 15, 2015, provisional application No. 62/276,047, filed on Jan. 7, 2016, provisional application No. 62/295,306, filed on Feb. 15, 2016, provisional application No. 61/390,982, filed on Oct. 7, 2010, provisional application No. 61/569,145, filed on Dec. 9, 2011, provisional application No. 61/697,204, filed on Sep. 5, 2012, provisional application No. 61/717,441, filed on Oct. 23, 2012, provisional application No. 61/729,149, filed on Nov. 21, 2012, provisional application No. 61/808,455, filed on Apr. 4, 2013, provisional application No. 61/822,081, filed on May 10, 2013, provisional application No. 61/808,455, filed on Apr. 4, 2013, provisional application No. 61/822,081, filed on May 10, 2013.

(51) Int. Cl.

| | | |
|---|---|---|
| F04B 43/00 | (2006.01) | |
| B01L 3/00 | (2006.01) | |
| A01N 1/02 | (2006.01) | |
| C12M 3/00 | (2006.01) | |
| C12M 1/32 | (2006.01) | |
| C12M 1/00 | (2006.01) | |
| C12M 1/34 | (2006.01) | |
| F04B 19/00 | (2006.01) | |
| C12M 1/12 | (2006.01) | |
| F04B 43/12 | (2006.01) | |

(52) U.S. Cl.
CPC .......... *C12M 23/44* (2013.01); *C12M 23/58* (2013.01); *C12M 25/02* (2013.01); *C12M 29/00* (2013.01); *C12M 29/10* (2013.01); *C12M 41/36* (2013.01); *C12M 41/48* (2013.01); *F04B 19/006* (2013.01); *F04B 43/0045* (2013.01); *F04B 43/12* (2013.01); *B01L 3/502715* (2013.01)

(58) Field of Classification Search
CPC ..... C12M 41/48; C12M 41/36; B01L 3/5027; B01L 3/502715; A01N 1/0247
See application file for complete search history.

(56) References Cited

OTHER PUBLICATIONS

Calligaris, D., et al. (2013). "Mass spectrometry imaging as a tool for surgical decision-making." Journal of Mass Spectrometry 48(11): 1178-1187.

Chaurand, P., et al. (2002). "Imaging mass spectrometry: a new tool to investigate the spatial organization of peptides and proteins in mammalian tissue sections." Current Opinion in Chemical Biology 6(5): 676-681.

Comi, T. J., et al. (2017). "MALDI MS Guided Liquid Microjunction Extraction for Capillary Electrophoresis-Electrospray Ionization MS Analysis of Single Pancreatic Islet Cells." Analytical Chemistry 89(14): 7765-7772.

de Macedo, C. E. A., et al. (2016). Brain Microdialysis. Rodent Model as Tools in Ethical Biomedical Research. M. L. Andersen and S. Tufik. Cham, Springer International Publishing: 217-233.

Dhunna, M. (2015). Desorption Electrospray Ionization Mass Spectrometry Imaging: Instrumentation, Optimization and Capabilities. Chemistry and Biochemistry. Provo, Utah, Brigham Young University. MS.

Dunham, S. J. B., et al. (2017). "Mass Spectrometry Imaging of Complex Microbial Communities." Accounts of Chemical Research 50(1): 96-104.

Eberlin, L. S., et al. (2011). "Desorption electrospray ionization mass spectrometry for lipid characterization and biological tissue imaging." Biochimica Et Biophysica Acta-Molecular and Cell Biology of Lipids 1811(11): 946-960.

Enders, J. R., et al. (2010). "Towards monitoring real-time cellular response using an integrated microfluidics-MALDI/NESI-ion mobility-mass spectrometry platform." IET Systems Biology 4(6): 416-427.

Enders, J. R., et al. (2012). "A Dual-Column Solid Phase Extraction Strategy for Online Collection and Preparation of Continuously Flowing Effluent Streams for Mass Spectrometry." Analytical Chemistry 84(20): 8467-8474.

Fried, I., et al. (1999). "Cerebral microdialysis combined with single-neuron and electroencephalographic recording in neurosurgical patients—Technical note." Journal of Neurosurgery 91(4): 697-705.

Gill, E. L., et al. (2017). "Monitoring Dopamine ex Vivo during Electrical Stimulation Using Liquid-Microjunction Surface Sampling." Analytical Chemistry 89(24): 13658-13665.

Girod, M., et al. (2010). "Desorption Electrospray Ionization Imaging Mass Spectrometry of Lipids in Rat Spinal Cord." Journal of the American Society for Mass Spectrometry 21(7): 1177-1189.

Griffiths, R. L., et al. (2018). "Ambient surface mass spectrometry-ion mobility spectrometry of intact proteins." Current Opinion in Chemical Biology 42: 67-75.

Griffiths, R. L., et al. (2017). "Raster-Mode Continuous-Flow Liquid Microjunction Mass Spectrometry Imaging of Proteins in Thin Tissue Sections." Analytical Chemistry 89(11): 5684-5688.

Ifa, D. R. and L. S. Eberlin (2016). "Ambient Ionization Mass Spectrometry for Cancer Diagnosis and Surgical Margin Evaluation." Clinical Chemistry 62(1): 111-123.

Kertesz, V., et al. (2005). "Automation of a surface sampling probe/electrospray mass spectrometry system." Analytical Chemistry 77(22): 7183-7189.

Kertesz, V. and G. J. Van Berke (2013). "Automated liquid microjunction surface sampling-HPLC-MS/MS analysis of drugs and metabolites in whole-body thin tissue sections." Bioanalysis 5(7): 819-826.

Kertesz, V. and G. J. Van Berkel (2010). "Fully automated liquid extraction-based surface sampling and ionization using a chip-based robotic nanoelectrospray platform." Journal of Mass Spectrometry 45(3): 252-260.

Kertesz, V. and G. J. Van Berkel (2010). "Liquid Microjunction Surface Sampling Coupled with High-Pressure Liquid Chromatography-Electrospray Ionization-Mass Spectrometry for Analysis of Drugs and Metabolites in Whole-Body Thin Tissue Sections." Analytical Chemistry 82(14): 5917-5921.

Kumara, P. M., et al. (2016). "Desorption Electrospray Ionization (DESI) Mass Spectrometric Imaging of the Distribution of Rohitukine in the Seedling of Dysoxylum binectariferum Hook. F." PloS One 11(6).

Lane, A. L., et al. (2009). "Desorption electrospray ionization mass spectrometry reveals surface-mediated antifungal chemical defense of a tropical seaweed." Proceedings of the National Academy of Sciences of the United States of America 106(18): 7314-7319.

(56) References Cited

OTHER PUBLICATIONS

LeDuc, P. R., et al. (2011). "How do control-based approaches enter into biology?" Annual Review of Biomedical Engineering 13: 369-396.

Lee, J. K., et al. (2016). "High-Resolution Live-Cell Imaging and Analysis by Laser Desorption/Ionization Droplet Delivery Mass Spectrometry." Analytical Chemistry 88(10): 5453-5461.

Lorenz, M., et al. (2013). "Laser microdissection and atmospheric pressure chemical ionization mass spectrometry aoupled for multimodal imaging." Rapid Communications in Mass Spectrometry 27(13): 1429-1436.

MacVane, S. H., et al. (2014). "In vitro microdialysis membrane efficiency of broad-spectrum antibiotics in combination and alone." Clinical Pharmacology: Advances and Applications 6: 97-101.

Marasco, C. C., et al. (2015). "Real-time Cellular Exometabolome Analysis with a Microfluidic-mass Spectrometry Platform." PloS One 10(2).

Monge, M. E. and F. M. Fernandes (2014). An Introduction to Ambient Ionization Mass Spectrometry. Ambient Ionization Mass Spectrometry M. Domin and R. Cody: 1-22.

Nguyen, S. N., et al. (2017). "Constant-Distance Mode Nanospray Desorption Electrospray Ionization Mass Spectrometry Imaging of Biological Samples with Complex Topography." Analytical Chemistry 89(2): 1131-1137.

Norris, J. L., et al. (2003). "Mass spectrometry of intracellular and membrane proteins using cleavable detergents." Analytical Chemistry 75(23): 6642-6647.

Ovchinnikova, O. S., et al. (2013). "Laser Ablation Sampling of Materials Directly into the Formed Liquid Microjunction of a Continuous Flow Surface Sampling Probe/Electrospray Ionization Emitter for Mass Spectral Analysis and Imaging." Analytical Chemistry 85(21): 10211-10217.

Pan, N., et al. (2015). "Single-Cell MS and High-Spatial-Resolution MS Imaging Under Ambient Conditions Using a Novel Sampling Device." Lc Gc North America 33(6): 414-419.

Quanico, J., et al. (2017). "NanoLC-MS coupling of liquid microjunction microextraction for on-tissue proteomic analysis." Biochimica Et Biophysica Acta-Proteins and Proteomics 1865(7): 891-900.

Rao, W., et al. (2016). "Applications of the Single-probe: Mass Spectrometry Imaging and Single Cell Analysis under Ambient Conditions." Jove-Journal of Visualized Experiments(112).

Sinclair, I., et al. (2016). "Novel Acoustic Loading of a Mass Spectrometer: Toward Next-Generation High-Throughput MS Screening." Journal of Laboratory Automation 21(1): 19-26.

Svatos, A. (2010). "Mass spectrometric imaging of small molecules." Trends in Biotechnology 28(8): 425-434.

Van Berkel, G. J. and V. Kertesz (2009). "Application of a Liquid Extraction Based Sealing Surface Sampling Probe for Mass Spectrometric Analysis of Dried Blood Spots and Mouse Whole-Body Thin Tissue Sections." Analytical Chemistry 81(21): 9146-9152.

Van Berkel, G. J. and V. Kertesz (2013). "Continuous-flow liquid microjunction surface sampling probe connected on-line with high-performance liquid chromatography/mass spectrometry for spatially resolved analysis of small molecules and proteins." Rapid Communications in Mass Spectrometry 27(12): 1329-1334.

Van Berkel, G. J., et al. (2008). "Liquid microjunction surface sampling probe electrospray mass spectrometry for detection of drugs and metabolites in thin tissue sections." Journal of Mass Spectrometry 43(4): 500-508.

Wisztorski, M., et al. (2017). Droplet-Based Liquid Extraction for Spatially-Resolved Microproteomics Analysis of Tissue Sections. Imaging Mass Spectrometry : Methods and Protocols. L. M. Cole. New York, NY, Springer New York: 49-63.

Nu, C. P., et al. (2013). "Mass spectrometry imaging under ambient conditions." Mass Spectrometry Reviews 32(3): 218-243.

Zheng, Q. L. and H. Chen (2016). Development and Applications of Liquid Sample Desorption Electrospray Ionization Mass Spectrometry. Annual Review of Analytical Chemistry. P. W. Bohn and J. E. Pemberton. 9: 411-448.

Bradberry, C. W., et al. (1991). "In vitro Microdialysis: A novel technique for stimulated neurotransmitter release measurements." Journal of Neuroscience Methods 36(1): 85-90.

Brown, J. A., et al. (2016). Metabolic consequences of inflammatory disruption of the blood-brain barrier in an organ-on-chip model of the human neurovascular unit, Journal of Neuroinflammation 13:306.

Brown, J. A., et al. (2015). Recreating blood-brain barrier physiology and structure on chip: A novel neurovascular microfluidic bioreactor, Biomicrofluidics 9: 054124.

Brown, J. A., et al. (2014). Metabolic Consequences of Interleukin-6 Challenge in Developing Neurons and Astroglia. Journal of Neuroinflammation 11:183.

Brown, K. J. et al. The human secretome atlas initiative: Implications in health and disease conditions. Biochim. Biophys. Acta—Proteins Proteomics 1834, 2454-2461 (2013).

Förster, Y. et al. Microdialysis Sampling from Wound Fluids Enables Quantitative Assessment of Cytokines, Proteins, and Metabolites Reveals Bone Defect-Specific Molecular Profiles. PLoS One 11, e0159580 (2016).

Hines, K. M., et al. (2013). "Biomolecular signatures of diabetic wound healing by structural mass spectrometry." Analytical Chemistry 85(7): 3651-3659.

* cited by examiner

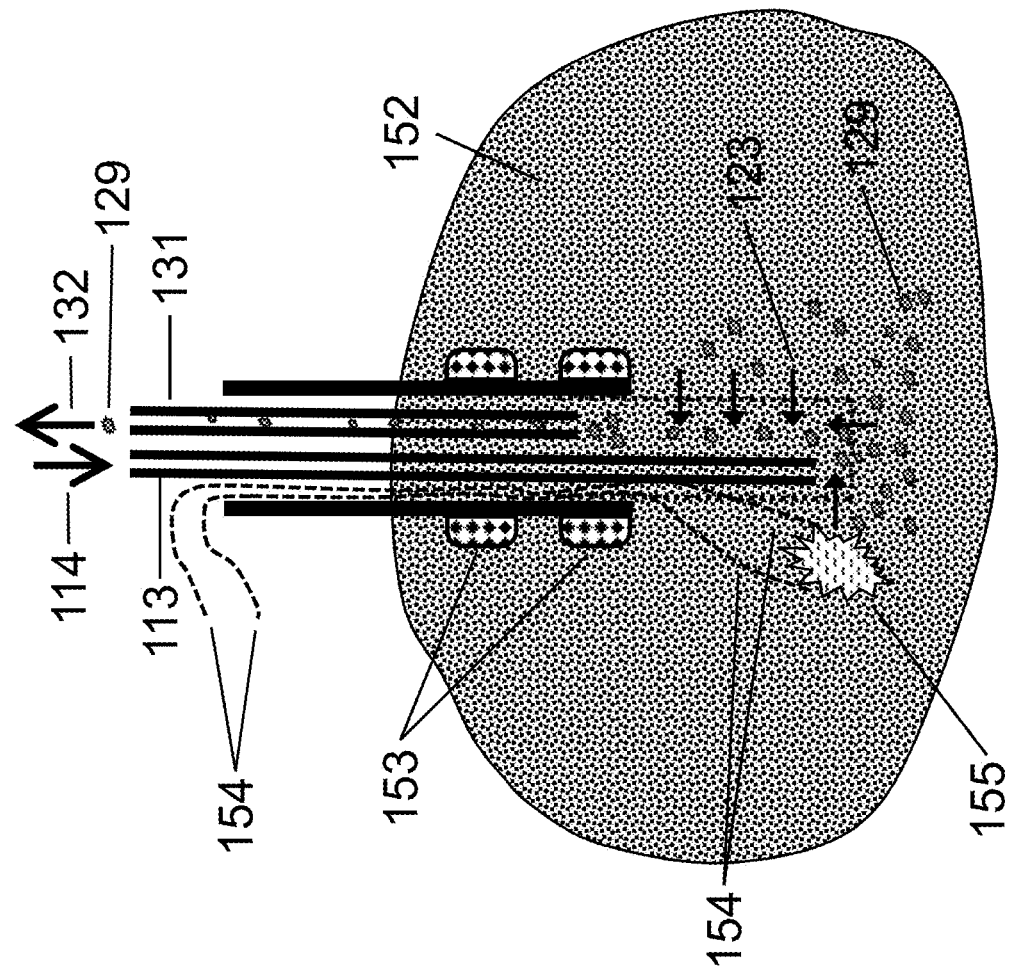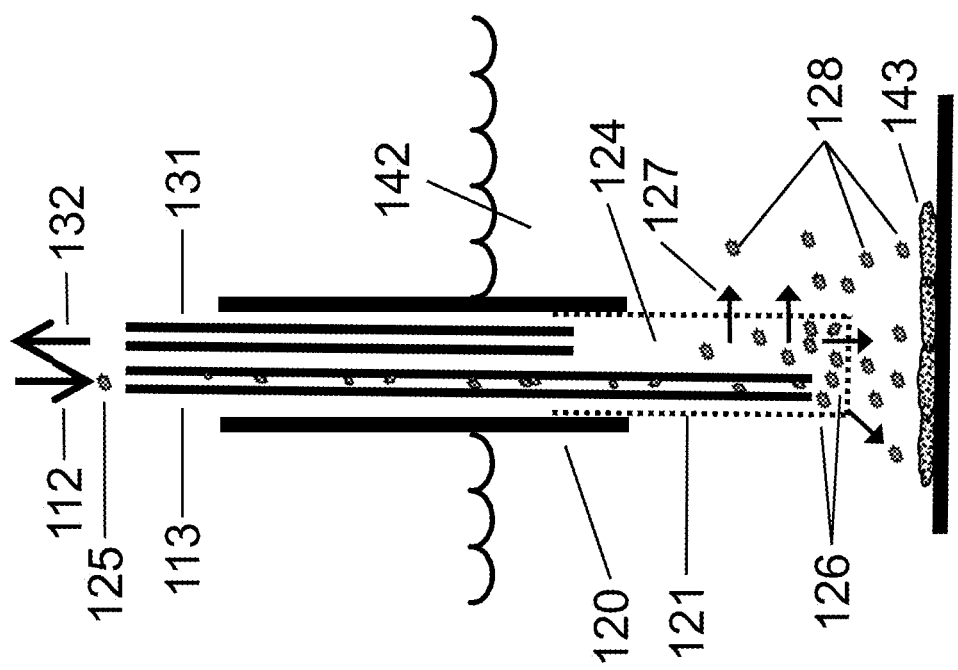

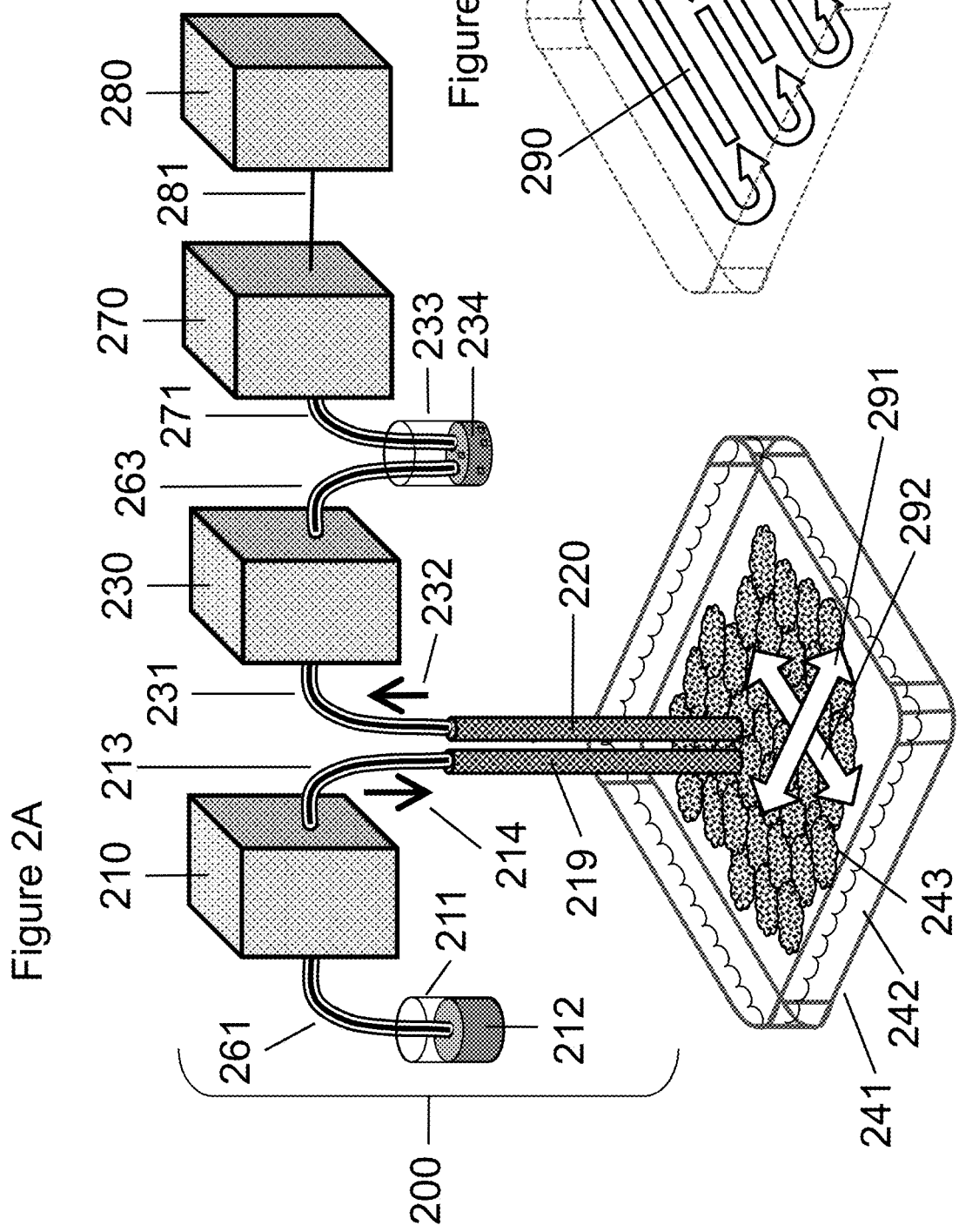

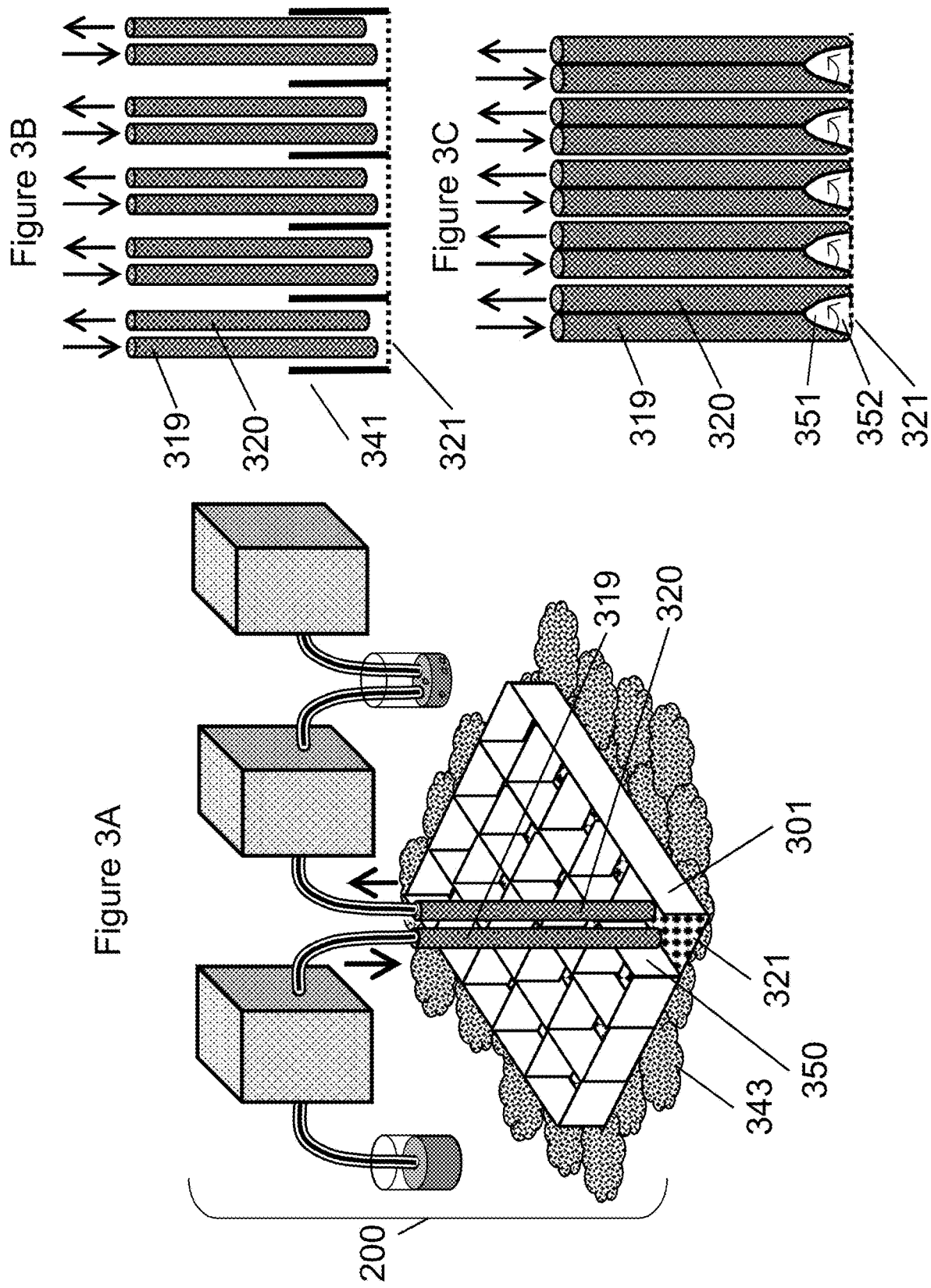

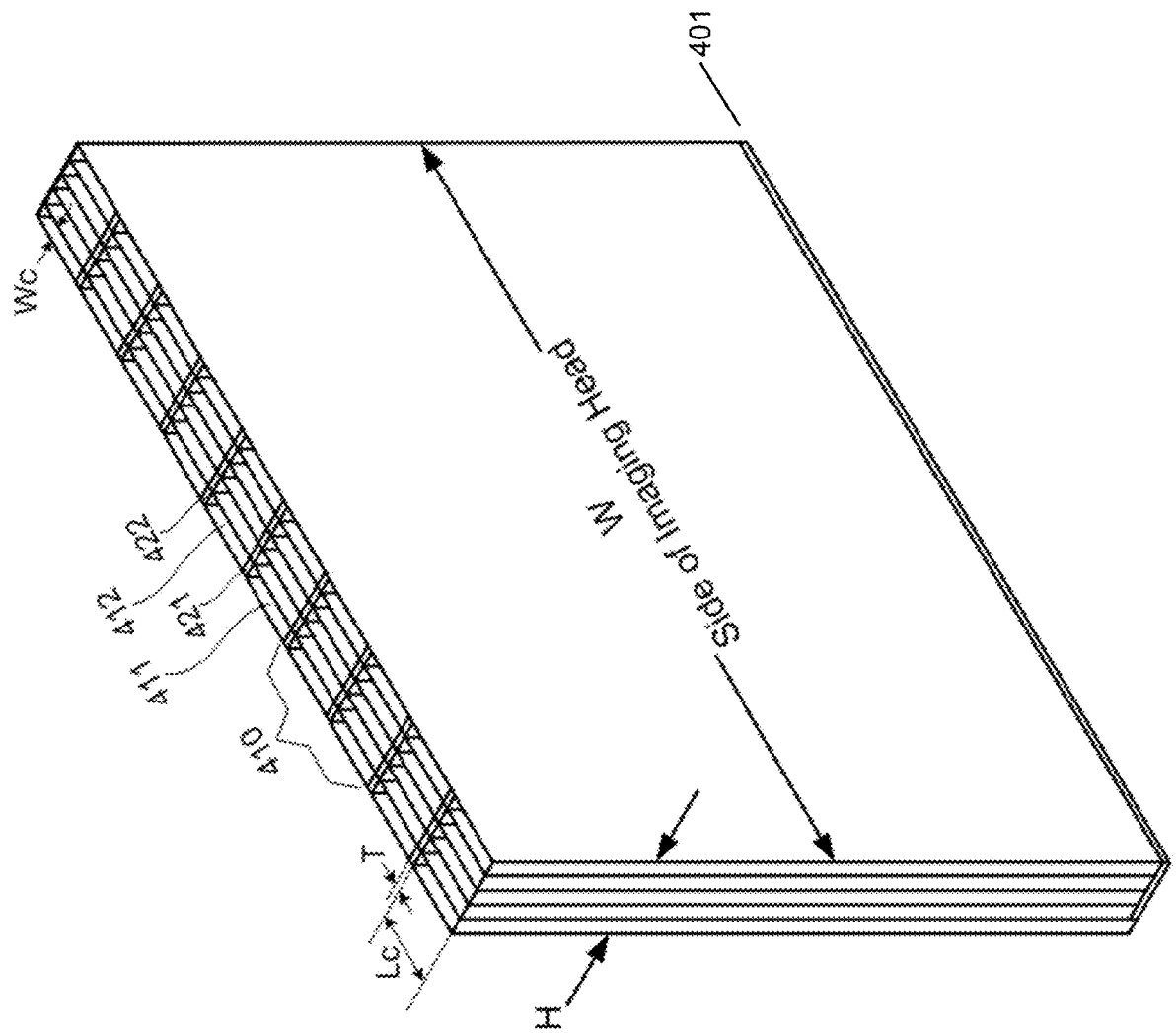
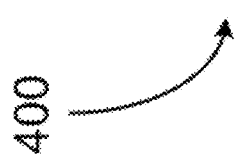
Figure 4A

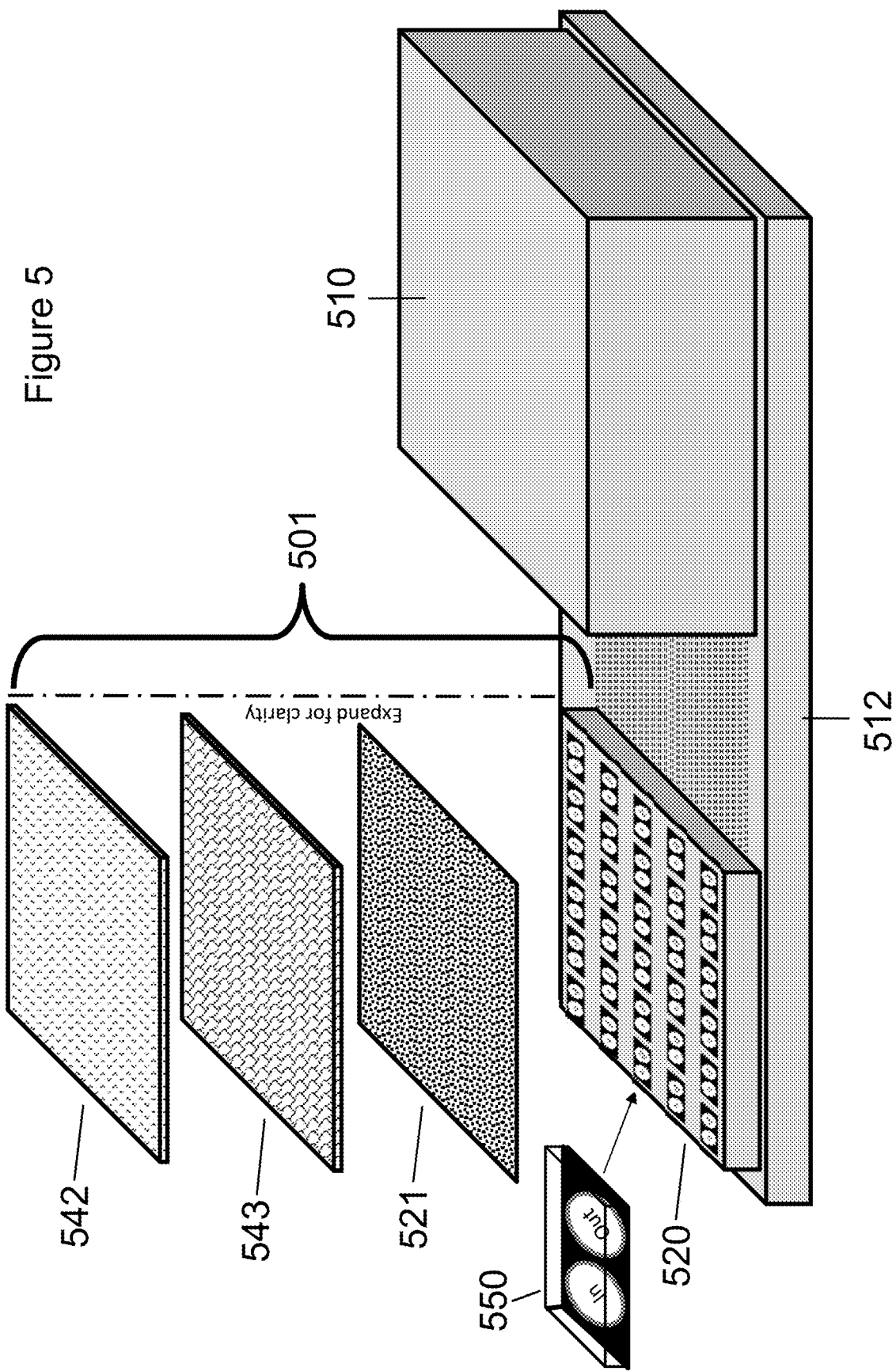

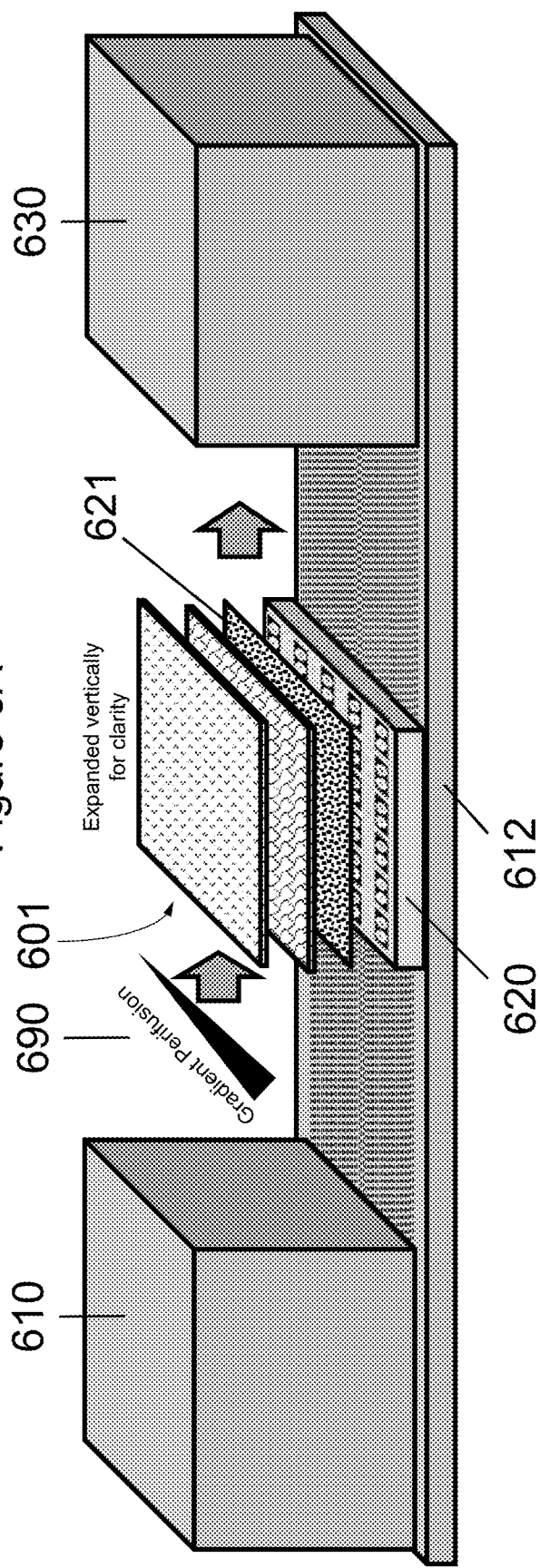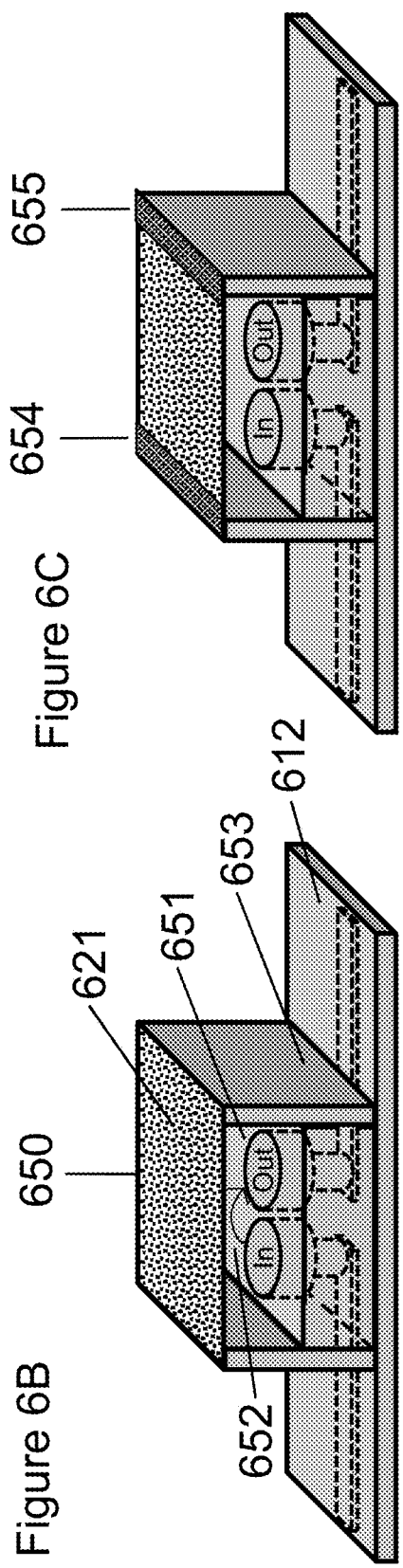

SYSTEM AND METHOD FOR MICRODIALYSIS IMAGING AND REGIONAL FLUIDIC DELIVERY AND CONTROL AND APPLICATIONS OF SAME

CROSS-REFERENCE TO RELATED PATENT APPLICATIONS

This application claims priority to and the benefit of U.S. Provisional Patent Application Ser. No. 62/664,499, filed Apr. 30, 2018.

This application is also a continuation-in-part application of U.S. patent application Ser. No. 16/012,900, filed Jun. 20, 2018, which is a divisional application of U.S. patent application Ser. No. 15/191,092 (the '092 application), filed Jun. 23, 2016, now U.S. Pat. No. 10,023,832, which claims priority to and the benefit of U.S. Provisional Patent Application Ser. Nos. 62/183,571, 62/193,029, 62/276,047 and 62/295,306, filed Jun. 23, 2015, Jul. 15, 2015, Jan. 7, 2016 and Feb. 15, 2016, respectively. The '092 application is also a continuation-in-part application of U.S. patent application Ser. No. 13/877,925 (the '925 application), Ser. No. 14/363,074 (the '074 application), Ser. No. 14/646,300 (the '300 application) and Ser. No. 14/651,174 (the '174 application), filed Jul. 16, 2013, Jun. 5, 2014, May 20, 2015 and Jun. 10, 2015, respectively. The '925 application, now abandoned, is a national stage entry of PCT Application Serial No. PCT/US2011/055432, filed Oct. 7, 2011, which claims priority to and the benefit of U.S. Provisional Patent Application Ser. No. 61/390,982, filed Oct. 7, 2010. The '074 application, now U.S. Pat. No. 10,078,075, is a national stage entry of PCT Application Serial No. PCT/US2012/068771, filed Dec. 10, 2012, which claims priority to and the benefit of U.S. Provisional Patent Application Ser. Nos. 61/569,145, 61/697,204 and 61/717,441, filed Dec. 9, 2011, Sep. 5, 2012 and Oct. 23, 2012, respectively. The '300 application, now U.S. Pat. No. 9,874,285, is a national stage entry of PCT Application Serial No. PCT/US2013/071026, filed Nov. 20, 2013, which claims priority to and the benefit of U.S. Provisional Patent Application Ser. Nos. 61/729,149, 61/808,455, and 61/822,081, filed Nov. 21, 2012, Apr. 4, 2013 and May 10, 2013, respectively. The '174 application, now U.S. Pat. No. 9,618,129, is a national stage entry of PCT Application Serial No. PCT/US2013/071324, filed Nov. 21, 2013, which claims priority to and the benefit of U.S. Provisional Patent Application Ser. Nos. 61/808,455 and 61/822,081, filed Apr. 4, 2013 and May 10, 2013, respectively.

Each of the above-identified application is incorporated herein by reference in its entirety.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [1] represents the first reference cited in the reference list, namely, Block III, F. E., et al. (2017). Normally closed microvalve and applications of the same. U.S. Pat. No. 9,618,129, Vanderbilt University.

STATEMENT AS TO RIGHTS UNDER FEDERALLY-SPONSORED RESEARCH

This invention was made with government support under Contract Nos. 1UG3TR002097-01 and HHSN271201700044C awarded by the National Institutes of Health. The government has certain rights in the invention.

FIELD OF THE INVENTION

The invention relates generally to dialysis, and more particularly to a system and method for microdialysis imaging and regional fluidic delivery and control for dialyzing/retrodialyzing/culturing/controlling/analyzing the living bio-object and applications of the same.

BACKGROUND INFORMATION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Dialysis is the chemical process by which particles in a liquid, such as organic or inorganic molecules of various sizes and properties, are separated based upon differences in their ability to pass through the pores of a semipermeable membrane. In medicine, dialysis refers to the clinical purification of blood by allowing excess water, urea, and other waste molecules in the blood to cross, by passive diffusion, down a concentration gradient and across the semipermeable membrane, from a region of high concentration (the blood) to a solution of pure water, electrolytes, and salts, termed the dialysate. Within the dialysis system, dialysate delivered to the membrane has a low concentration of the waste products and, if excess water is to be removed from the blood, a higher osmolarity to support the diffusion of water across the membrane into the dialysate. As the concentration of the chemical species to be dialyzed increases within the dialysate contained by the membrane, that dialysate is replaced with fresh dialysate so that dialysis can proceed unimpeded.

In the case of kidney dialysis as a substitute for the normal function of the kidney, the purpose of the dialysate is to pull toxins and excess water from the blood into the dialysate by diffusion down a concentration gradient that is supported by a semi-permeable membrane that, if desired, can be impermeable to large molecules in blood such as albumin.

Microdialysis is a functionally equivalent process using a small cylindrical probe with a semipermeable membrane at its end to collect for analysis specific chemicals released by cells in a small region of the intact brain, for example, or cells being cultured in a Petri dish. There is a substantial body of literature on microdialysis of the brain [6, 44]. An excellent example of in vitro microdialysis is provided by MacVane et al. [27]. Brain microdialysis works through diffusing molecules through a semipermeable membrane which is located at the tip of the probe. There are two modes associated with the process, dialysis where molecules are removed from the system for analysis, and retrodialysis where molecules such as a drug are delivered to the biological system under study. Both modes are a result of diffusion that causes molecules to be transported from the inside of the tip into the brain microenvironment and other to molecules in the brain microenvironment to be transported by diffusion to the inside of the tip.

In addition to the microdialysis as described above, there are a wide variety of other methods to perform the collection and analysis of the chemicals associated with a living or fixed biological sample such as the cells. Imaging mass spectrometry (matrix assisted laser desorption ionization (MALDI MS)) places the fixed or frozen samples in vacuum and uses a scanning laser to ionize chemical species in the matrix-coated sample [2, 3, 31]. There is a growing literature on air-sampling mass spectrometry, e.g., desorption electrospray ionization (DESI) and liquid junction mass spectrometry and other related techniques [3, 5, 7-9, 13-23, 25, 26, 29-43].

All of these air-sampling approaches utilize a single point collection probe that is placed adjacent to a horizontal or vertical sample. The delivery probe may deliver solvent, ionized gas, deionized water or other liquids, desorption matrix, and/or laser light to the sample, or may not be required for a particular analysis approach. It is also possible to utilize acoustic loading to deliver a sample of fluid from a well plate or dish directly to a mass spectrometer [36].

When trying to determine the spatiotemporal nature of gene-regulatory and metabolic signaling and control networks, the aforementioned point-sampling approaches have a significant disadvantage: while the collection probe is gathering analyte from a particular location for subsequent analysis, the adjacent locations are biologically active and are both consuming and releasing chemicals to support their metabolic and signaling activities, which, in the case of heterogeneous tissues of common interest, may have a substantially different temporal composition profile than the adjacent region being sampled at that time.

For low concentration signals, the analyte not being detected is lost by diffusive or advective mixing into the bulk media surrounding the sample while analyte is being detected at another location. In addition, the ability to sample only one location at a time provides an incomplete description of the chemical activity at that region that has occurred since the previous time it was sampled. The signal at one location is not being integrated over time, and there is a risk of under-sampling of the concentration time profile with the concomitant risk of violating the Shannon/Nyquist sampling theorem and producing temporally aliased concentration profiles.

Therefore, a heretofore unaddressed need exists in the art to address the aforementioned deficiencies and inadequacies.

SUMMARY OF THE INVENTION

In one aspect, the invention relates to a system for microdialysis imaging and regional fluidic delivery and control for dialyzing/retrodialyzing/culturing/controlling/analyzing the living bio-object. The living bio-object includes cells, tissues, or an organ of a living subject.

In one embodiment, the system includes a microdialysis imager including a imaging head having N pixels aligned in a pixel array for monitoring a state of a living bio-object that is in fluidic communication with the pixel array, N being a positive integer greater than one; and a fluidic module coupled to the microdialysis imager for delivering a fluidic substance to and collecting effluent from the living bio-object. The fluidic module includes a fluidic network having a plurality of valves, a plurality of fluidic channels in fluidic communication with the plurality of valves and one or more pumps coupled to corresponding fluidic channels, and a microcontroller coupled to the fluidic network for individually controlling the plurality of valves and the one or more pumps of the fluidic network as so to operably and selectively deliver the fluidic substance to and continuously collect the effluent from the living bio-object responsive to the delivered fluidic substance via each pixel of the pixel array in real time.

In one embodiment, the system further includes an analyzer unit coupled to the at least one multi-channel output director valve of the collection control unit. In one embodiment, the analyzer unit includes among various chemical detectors either a fluorimeter, an electrochemical analyzer, a capillary electrophoresis detector, a liquid chromatography detector, a radiation detector, an impedance/conductance analyzer, a mass spectrometer, etc., or some combination thereof.

In one embodiment, the microdialysis imager further includes a microdialysis membrane, also known as the semipermeable membrane, on the imaging head for placing the living bio-object thereon; and a layer of cell culture or perfusion media disposed on the microdialysis membrane. The cell culture or perfusion media would serve as a means that would support the diffusion of chemicals to and from the cells to the microdialysis membrane.

In one embodiment, the microdialysis imager is in fluidic communication with the plurality of fluidic channels via the second end of the pixel array.

In one embodiment, the delivery of the fluidic substance to and the collection of the effluent from the living bio-object in each pixel of the pixel array are via the second end of the pixel array.

In one embodiment, the first and second ends of the pixel array are top and bottom ends of the pixel array, respectively, so that the microdialysis imager is in an inverted geometry.

In one embodiment, the microdialysis imager further includes a microelectrode array (MEA) superimposed on the semipermeable membrane, where the MEA is corresponding to the pixel array with each pair of electrodes coupled to a respective pixel for detecting electrical activity of the living bio-object in an immediate vicinity of the respective pixel.

In one embodiment, the MEA is provided as a substrate disposed between the cells/tissues and the semipermeable/microdialysis membrane, where the substrate has through holes, each through hole being corresponding to a respective underlying pixel to allow fluidic communication with the respective underlying microdialysis pixel to enable detection of cellular chemical signals, and where the electrodes are connected to detection electronics by thin-film leads to enable detection of cellular electrical signals.

In one embodiment, the semipermeable membrane is made of polyarylonitrile, AN69, cuprophane, polycarbonate, polyamide, polysufone, polyarylethersulfone, or a combination thereof.

In one embodiment, each valve is a rotary planar valve (RPV), and each pump is a rotary planar peristaltic micropump (RPPM).

In one embodiment, the fluidic module includes a delivery control unit disposed on one side of the microdialysis imager, and a collection control unit disposed on the other side of the microdialysis imager, where the delivery control unit, the microdialysis imager and the collection control unit are in fluidic communication with each other, so that input and output of each pixel of the pixel array are operably controllable by the delivery control unit and/or the collection control unit.

In one embodiment, the delivery control unit includes at least one multi-channel input selector valve coupled to a plurality of input ports that operably provides a plurality of fluids, at least one input pump coupled to the at least one multi-channel input selector valve, and at least one multi-channel input director valve coupled to the at least one input pump; the collection control unit includes at least one multi-channel output collector valve, at least one output pump coupled to the at least one multi-channel output collector valve and at least one multi-channel output director valve; and the microdialysis imager is coupled between the at least one multi-channel input director valve of the delivery control unit and the at least one multi-channel output collector valve of the collection control unit.

In one embodiment, the fluidic module is configured such that the fluidic substance delivered to the living bio-object is identical in each pixel of the pixel array, or different in different pixels of the pixel array. In one embodiment, the fluidic substance contains one or more fluids with a concentration of each fluid controllable in real time. In one embodiment, the fluidic substance has a one-dimensional or two-dimensional concentration gradient distribution across the pixel array.

In another aspect, the invention relates to a method for microdialysis imaging and regional fluidic delivery and control for dialyzing/retrodialyzing/culturing/controlling/analyzing the living bio-object. The living bio-object includes cells, tissues, or an organ of a living subject.

In one embodiment, the method includes providing a microdialysis imager and a fluidic network, where the microdialysis imager includes a imaging head having N pixels aligned in a pixel array for monitoring a state of the living bio-object that is in fluidic communication with the pixel array, N being a positive integer greater than one, and where the fluidic network is coupled to the microdialysis imager and a plurality of fluids and includes a plurality of valves, a plurality of fluidic channels in fluidic communication with the plurality of valves, and one or more pumps coupled to corresponding fluidic channels; and individually controlling the plurality of valves and the one or more pumps of the fluidic network to operably and selectively deliver a fluidic substance to and continuously or intermittently collect the effluent from the living bio-object responsive to the delivered fluidic substance via each pixel of the pixel array in real time, where the fluidic substance contains one or more of the plurality of fluids.

In one embodiment, each pixel includes a delivery channel and a collection channel in fluidic communication with each other, and each of the delivery and collection channels of each pixel is in a round, square, rectangular, hexagonal, or other-shaped crossection tube or chamber whose open end area defines a pixel area.

In one embodiment, the controlling step includes controlling the fluidic substance delivered to the living bio-object to be identical in each pixel of the pixel array, or to be different in different pixels of the pixel array.

In one embodiment, the controlling step includes controlling the fluidic substance to have a concentration of each fluid being constant or varying with time.

In one embodiment, the controlling step includes controlling the fluidic substance to have a one-dimensional or two-dimensional concentration gradient distribution across the pixel array.

In one embodiment, the fluidic substance contains perfusate or drugs, toxins, nutrients, growth factors and other endogenous and exogenous chemical species, and the effluent contains dialysate or waste as well as drug and toxin metabolites and signaling molecules from the living bio-object.

In one embodiment, the controlling step includes parallel pixel delivery of the fluidic substance, parallel pixel collection and storage of the effluent from each individual pixel, and serial pixel readout of the effluent.

In one embodiment, the controlling step includes M clock steps, M being a positive integer equal to or less than N, where in each clock step, a single aliquot of the fluidic substance is delivered sequentially to each pixel in N pixel steps, such that at any time, each pixel contains a different number of aliquots so that only one pixel is ready for analysis in each clock step, and then the aliquots in that pixel are collected for analysis, and the delivery and collection process in each clock step is repeated for all M clock steps, so that after the Nth aliquot is delivered to a pixel and allowed to dialyze the living bio-object, the N aliquots are then collected and transferred to an analyzer, and a single, fresh, aliquot is left in that pixel to start a new full cycle. In one embodiment, during N full cycles, the effluent of each pixel is transferred to the analyzer as a single bolus containing N aliquots.

In one embodiment, the method further includes analyzing the effluent so as to monitor the state of the living bio-object.

In one embodiment, the method further includes providing demarcation between a bolus of the effluent that is delivered to the analyzer from different pixels. In one embodiment, the step of providing demarcation includes injecting a bubble of air between boluses of the effluent from different pixels, so that the end of one bolus of the effluent and the beginning of another bolus of the effluent are detectable by a bubble detector.

In one embodiment, the fluidic channels are treated in a manner to make them hydrophobic to minimize the adhesion of a film of water to the channel that remains as the bubble moves along the channel to separate boluses.

In one embodiment, two boluses of effluent can be separated by two or more bubbles of air which in turn are separated by clean media or dialysate to minimize the cross-contamination between boluses gathered from different pixels.

In one embodiment, each valve in the system has the capability of being back-flushed to cross-contamination between either different mixtures of dialysate and drugs and other chemicals being delivered to different pixels, or boluses of dialysate gathered from different pixels.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 1A-1D show schematically a microdialysis and how a traditional concentric microdialysis probe works.

FIGS. 2A-2B show schematically further generalization of a conventional chemical imaging system that allows the dialysis probe to be scanned across the bio-object.

FIGS. 3A-3C show schematically a system for parallelizing the sampling process according to one embodiment of the invention.

FIGS. 4A-4B show schematically a microdialysis imager according to one embodiment of the invention.

FIG. 5 shows schematically a system for microdialysis imaging and regional fluidic delivery and control for dialyzing/retrodialyzing/culturing/controlling/analyzing the living bio-object according to one embodiment of the invention.

FIGS. 6A-6E show schematically system for microdialysis imaging and regional fluidic delivery and control for dialyzing/retrodialyzing/culturing/controlling/analyzing the living bio-object according to one embodiment of the invention.

FIG. 8A-8C shows a process for pixel loading and analysis for microdialysis imaging and regional fluidic delivery and control for dialyzing/retrodialyzing/culturing/controlling/analyzing the living bio-object according to embodiments of the invention.

DETAILED DESCRIPTION OF THE INVENTION

Figure 1B:
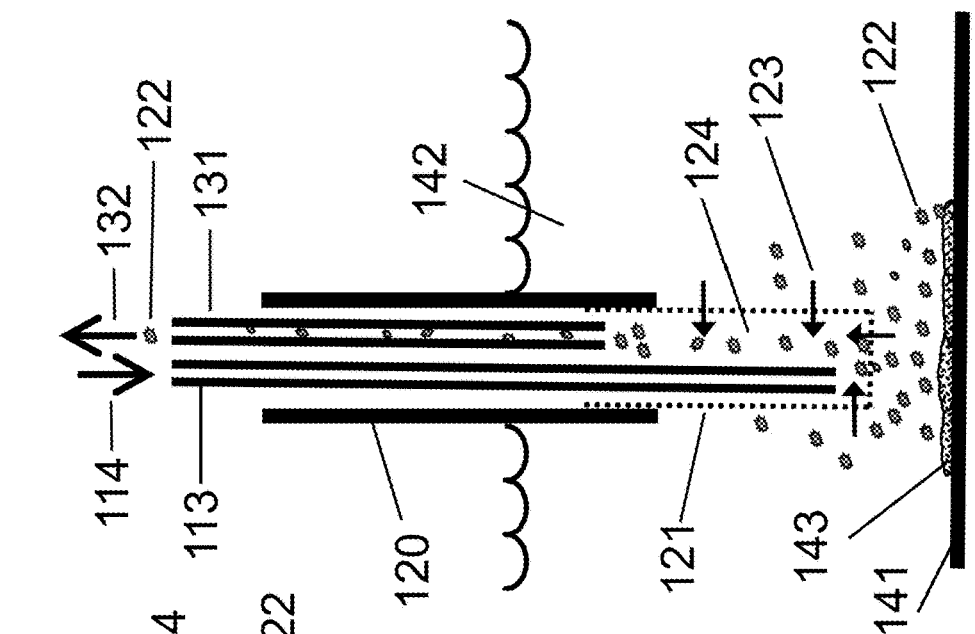

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used in this invention, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

One of the objectives of this invention is to provide system and method to acquire two-dimensional chemical images of living cells and tissues that are contained in an aqueous environment. The system in one embodiment has five components: a microfluidic delivery system that provides both gradients and point-wise delivery of chemicals to the cultured cells in real time, a microdialysis imager for monitoring the state of multiple pixels in the fluidic medium immediately exterior to the living system in real time, a microfluidic collection system that gathers separately the contents of each pixel, a chemical analyzer to detect and quantify the chemical composition of the contents of each pixel, and a computational system implementing a scheme for the analysis and closed-loop control of system state and chemical delivery.

According to the invention, a user can employ the microfluidic delivery system to supply an arbitrary combination of chemical signals to individual pixels at arbitrary times and in arbitrary amounts. Combining the microdialysis imager's measurement of a system state with the computational system's analysis of the system state can tell the user which chemical signals might need to be supplied next in real time to achieve a particular functional target, and supply the needed control chemicals without human intervention to move the system towards that target.

The invention is envisioned to be generally applicable to studying cellular differentiation and development, tissue maturation, cell-cell communication, wound healing, and the responses of cultured cells and tissue slices to applied chemical, electrical, and mechanical stimuli. In principle, the invention is applicable to studying cells from any tissue/organism. The control scheme can use a data-driven approach to teach itself how to work with any given organism, and the microdialysis imager is a general measurement device, so neither needs to be modified by hand to work in different contexts.

Figure 1A:
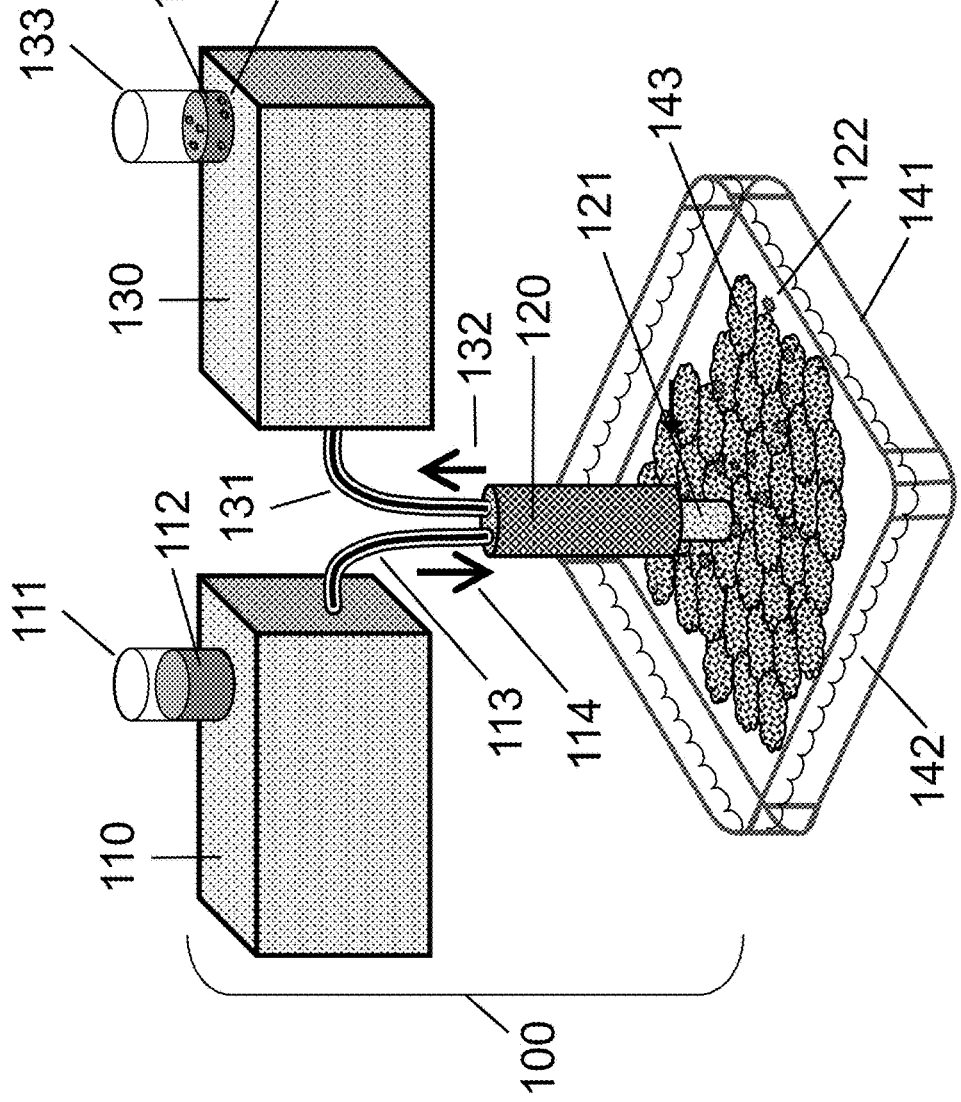

FIGS. 1A-1D illustrate how a traditional concentric microdialysis probe works. As shown in FIG. 1A, a microdialysis system 100 includes a pump unit 110, a probe 120, and a sample collection unit 130 that are, in this example, sampling the media 142 adjacent to cultured cells 143 in a Petri dish 141. The pump unit 110 has a dialysate reservoir 111 that delivers clean dialysate 112, also termed perfusate, to a microdialysis probe 120 via the delivery tube 113 that allows the perfusate to flow 114 from the reservoir to the interior of the cylindrical dialysis membrane 121. The sample collection unit 130 withdraws via collection tube 131 in direction 132 dialysate fluid with the chemicals that have diffused into the probe and deposits the sample of fluid 134 in collection reservoir 133. As shown in FIG. 1A, the chemical species 122 being sampled are secreted or metabolized by cells 143 cultured in cell culture media 142 in Petri dish 141. A chemical analyzer, not shown, would quantify the chemical constituents in the sample 134.

FIG. 1B shows a close-up of the concentric microdialysis probe 120 with its cylindrical outer shell. Chemical analyte species 122 are released by cells 143 in Petri dish 141 and then diffuse 123 through the cell culture medium 142. Because the concentration of these chemical species is lower in the dialysate 112 within the probe volume 124 than in the medium 142 outside of it, there is a net diffusion of the analyte across the semipermeable membrane 121 into the interior 124 of the probe. The flow 114 of fresh dialysate 112 and the coordinated withdrawal 132 of dialysate 134 from the probe volume 124 allows the subsequent quantitation of the analyte 122 by a variety of means, including fluorescence, electrochemical, chromatographic, mass spectrometric, radiation, impedance/conductance, and other means of detection (not shown).

FIG. 1C demonstrates the process of retrodialysis, in which a desired reagent, chemical, drug, toxin, growth factor, signaling molecule, or other exogenous compound 125 is added to the dialysate 112 that will be delivered to the probe 120, whereby that compound is presented at a higher concentration 126 within the semipermeable membrane and the probe volume 124 that it contains than the concentration of this substance 128 outside of the membrane, which in turn leads to outward diffusion 127 of this chemical species into the medium 142 that bathes the cells under study 143. By changing the concentration of the chemical 125 added to the dialysate over time, it is possible to change the concentration 128 of that chemical in the immediate vicinity of the cells over time, albeit with a time delay and temporal smoothing associated with the process of diffusion of the chemical across the semipermeable membrane and through the media in which the cells are cultured.

FIG. 1D shows how this probe can be inserted, often with the assistance of a hollow cannula (not shown), into the depth of the brain 152 of a living animal to detect, for example, neurotransmitters released by regional electrical activity in the brain that diffuse in the local intracellular space and the extracellular fluid that it contains. As demonstrated by Fried et al. [12], it is possible to add a pair of ring electrodes 153 around the probe to record the local electroencephalogram (EEG) of that region of the brain, and fine wire electrodes 154 to record the extracellular potentials generated by electrical signaling activity of individual neuronal units 155.

FIGS. 2A and 2B show a further generalization of a conventional chemical imaging system 200. There is a reagent delivery unit 210, an analyte collection unit 230, and an analyzer unit 270. The input reservoir 211 and the solution 212 it contains are connected to the input unit 210 by a tube 261. The fluidic output of the reagent delivery unit 210 is delivered by a tube 213 in a direction 214 to a delivery probe 219. The collection probe 220 moves the collected analyte in a direction 232 by a tube 231 to the analyte collection unit 230, which delivers the sampled analyte 234 to a sample reservoir 233 via a tube 263. The analyzer unit 270 withdraws the sample from the sample reservoir via a tube 271 and reports the concentration of the analytes to a computer 280 by wired or wireless connection 281.

As shown in FIG. 2A, it is possible to utilize an X-Y scanning stage (291 and 292) to position the delivery probe 219 and the detection probe 220 at an arbitrary location immediately adjacent to a living or fixed biological sample 249 that is maintained in water, air, vacuum, or another medium 242 for analysis. A wired or wireless connection (not shown) between the X-Y stage 291-292 and the computer 280 can, for example, be used for closed-loop control of the X-Y stage 291-292 in response to concentrations reported by the analyzer 270, for example to map the spatial gradient of a chemical signal released by a localized subpopulation of cells. A raster scan 290, as shown in FIG. 2B, can be used to create two-dimensional spatial images of distributions of different chemicals in the sample. Note that the concentration in each location will be measured only whenever the probe is over that particular location as defined by the scan 290.

Note that it is possible to simply remove fluid 242 from the medium bathing the cells by means of 220, 231, 232, and 230 without its localized replacement via the combination of 210, 213, 214, and 219. This will lead to a gradual reduction of the volume contained in the Petri dish 241, and an inward radial, advective flow of media 242 into the vicinity of the collection probe 220, thereby blurring any chemical gradients created by the living tissue/cells 243. Alternatively, even without the semipermeable membrane shown in FIGS. 1A-1D, the localized delivery of make-up media in the vicinity of the withdrawal probe could allow sampling with only local dilution of signaling compounds but without the advective flow associated with local fluid withdrawal without local fluid replacement. Note that there would still be localized concentration changes associated with the delivery of fluid to replace that which is withdrawn. One advantage of the use of the semipermeable/dialysis membrane in FIG. 1 is that it allows advective replacement of dialysate internal to the probe without inducing external advective flows, whereas in FIG. 2 the input and output probes are shown, for this particular embodiment, as being physically separated and not on the same side of a common dialysis membrane, as is the case in FIG. 1. The separate probes 219 and 220 in FIG. 2 could easily be replaced by the single probe 120 in FIG. 1 and be suitable for scanned microdialysis imaging.

When trying to determine the spatiotemporal nature of gene-regulatory and metabolic signaling and control networks, the aforementioned approaches have a significant disadvantage: while the collection probe is gathering analyte from a particular location for subsequent analysis, the adjacent locations are biologically active and are both consuming and releasing chemicals to support their metabolic and signaling activities, which, in the case of heterogeneous tissues of common interest, may have a substantially different temporal composition profile than the adjacent region being sampled at that time.

For low concentration signals, the analyte not being detected is lost by mixing into the bulk media surrounding the sample while analyte is being detected at another location. In addition, the ability to sample only one location at a time provides an incomplete description of the chemical activity at that region that has occurred since the previous time it was sampled. The signal at one location is not being integrated over time, and there is a risk of under-sampling of the concentration time profile with the concomitant risk of violating the Shannon/Nyquist sampling theorem and producing temporally aliased concentration profiles.

One solution to the problem is to simply utilize multiple sampling systems in parallel. FIG. 3A provides a system for parallelizing the sampling process according to one embodiment of the invention. A well plate or equivalent structure 301 with multiple chambers or wells 350 has as its lower surface a semipermeable membrane 321 that is placed adjacent to the living cells or tissue 343, with each well defining an individual pixel 350 that is microdialyzed or otherwise analyzed to create a time-dependent chemical image of the cells beneath the membrane. By minimizing the distance between the membrane 321 and the cells 343, the lateral diffusion between the regions beneath each pixel is minimized. A pair of delivery 319 and collection 320 probes is placed in a chosen well, and the sample is collected. A single probe could then be lifted up, moved to another well, and lowered down so that the microdialysis analysis process could be repeated until all wells in the plate 301 are sampled. Unfortunately, the accumulation of analyte in each well before it is sampled reduces the rate of dialysis and hence the amount of analyte that is available for quantitative analysis by the detection system.

Alternatively, there could be multiple probe pairs 319 and 320, in addition to the single pair shown, with each connected to a separate sample analysis module 200 functionally equivalent to the ones discussed above. Not only does this approach require a large number of redundant delivery, collection, and analysis modules, FIG. 3B shows another embodiment of the invention by means of a cross-section of the approach a major limitation: as the pixel size is decreased to below one millimeter, the minimum fabrication thickness of the walls of the both the well plate and the delivery and connection tubes limits the minimum size of the pixels and the volume of dialysate that they can contain.

To address the well-and-probe wall-thickness problem, FIG. 3C shows yet another embodiment of the invention where a single unit probe bonds the delivery tube 319 and the collection tube 320 together, with a gap 351 in the adjoining tube walls providing a connection between the two just above the semipermeable membrane 321 for the delivery and collection of the dialysis fluid above the membrane 321. Essentially, the bonded walls of the tubes serve as the dividing walls between the pixels, and the semipermeable membrane is bonded to the flattened lower surface of the collection of input and output tubes to create an array of microdialyzed pixels. While the probes shown in FIG. 3C each have a cylindrical cross-section, there would be better coverage of the sample and more efficient sampling of the analyte released by the cells were both probes to be square or rectangular in cross-section, such that the resulting pixel was either square or rectangular. Hexagonal pixels would also provide efficient spatial sampling of the bio-object 343. The key feature of this approach is that the gap 351 that connects the input probe 319 to the output probe 320 supports flow 352 across the probe-side of the semipermeable membrane 321. The rates of intermittent or slow-and-continuous flow of fresh dialysate into the probe region can be matched to optimize the rate of dialysis across the membrane 321.

Figure 4B:
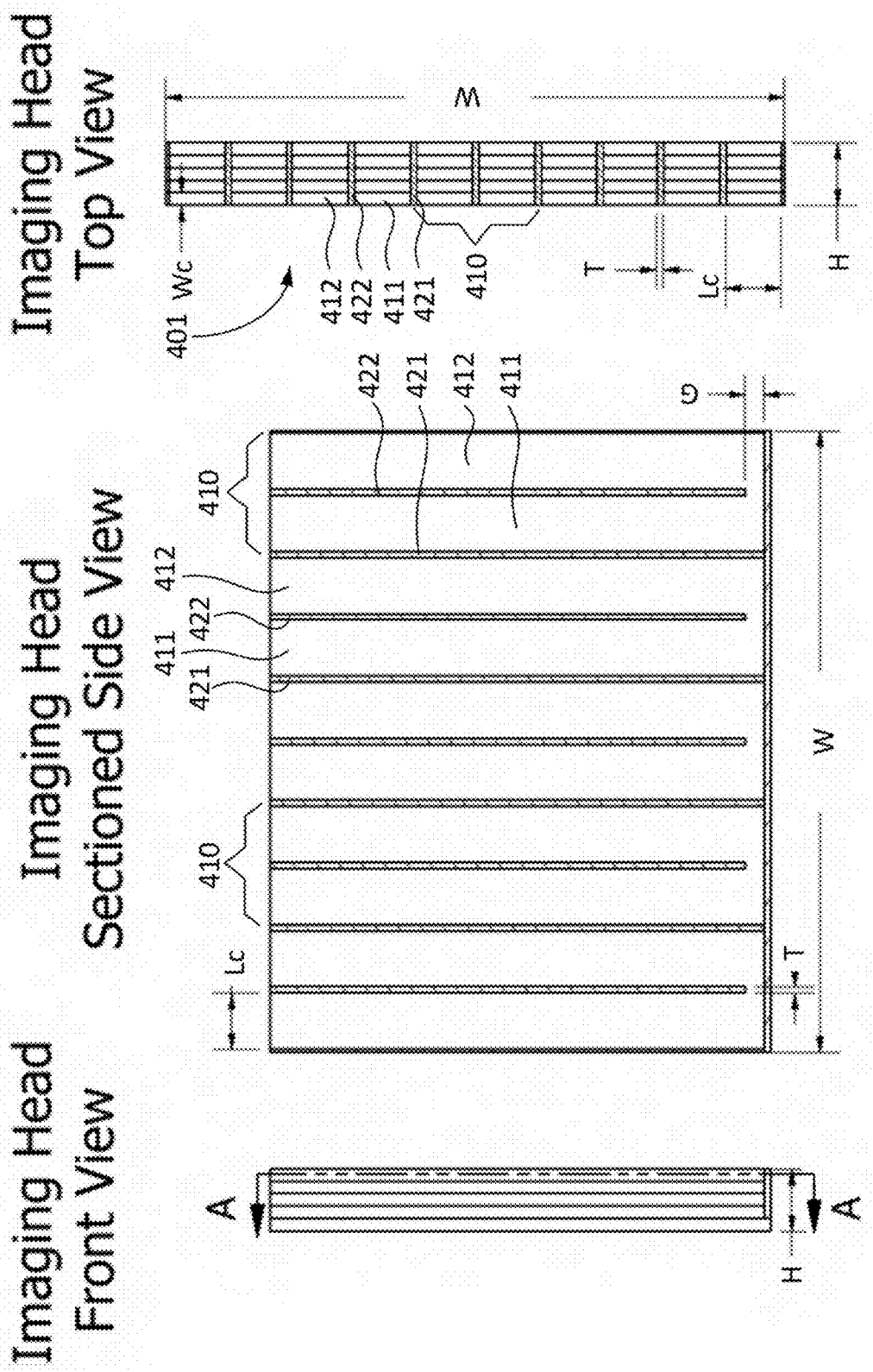

FIGS. 4A-4B show schematically a microdialysis imaging head (probe) 400 according to one embodiment of the invention, which includes twenty-five (25) pixels 410 aligned in a five-by-five array 401. With a wall (membrane) 421/422 having a thickness T=0.1 mm separating adjacent microfluidic channels 411 and 412 in a pixel plane 401, each channel 411/412 has a length $L_c$=0.9 mm and a width $W_c$=0.2 mm (ignoring the thickness of the membrane (wall) that separates the plane) and two channels 411 and 412 (delivery and withdrawal) create a single pixel 410 that has a pixel area (dimension) of about 2 mm×0.2 mm, which is consistent with the topology in FIG. 3C. In this embodiment, that vertical gap that allows fluidic communication between the delivery and collection channels 411 and 412 is G=0.3 mm. The design of this microdialysis imaging head 400 emulates the traditional topology of microdialysis probes, except with microfluidics and in a massively parallel format. The individual microdialysis tubes (i.e., channels) 411/412 within the imaging head 400 are no longer concentric. In certain embodiments, a planar set of tube pairs (ten channels total) is fabricated as a ribbon fluidic, and five of these layers are bonded to create the five-by-five imaging camera or array. In the exemplary embodiment shown in FIGS. 4A-4B, the five-by-five imaging camera or array has a width W=10 mm and a thickness H=1 mm. It should be appreciated that any numbers of channels per layer and/or any numbers of layers can be utilized to produce an imaging array of any desired spatial resolution in accordance with the invention. The imaging head itself dould be scanned to record from a larger area of a bio-object that is larger than the head. In addition, it should be noted that the dimensions (sizes) of the channels and the walls separating adjacent microfluidic channels disclosed in the above exemplary embodiment are illustrative only and in no way limit the scope and meaning of the invention, and other sizes of the channels and the walls can also be utilized to practice the invention.

In this exemplary example, each ribbon includes five pairs of tubes (i.e., channels), in each pair, one for delivery of perfusate and the other for removal of the dialysate. In the case of retrodialysis, the delivery provides the chemical species that diffuse into the biological sample under test. The delivery tube serves to introduce new molecules, transcription factors, drugs, toxins, and nutrients to the system through diffusion (retrodialysis), and the withdrawal tube removes molecules, secreted factors, and waste from the system for analysis by mass spectrometry, fluorescence detection, electrochemical sensing, or other means for detecting the presence of a chemical species in a fluid sample. As shown in FIGS. 3C and 4A-4B, for each pair of tubes 411 and 412 the perfusate delivery tube is on the left of each pair while the dialysate withdrawal tube is on the right. It should be noted that for each pair of tubes 411 and 412 the perfusate delivery tube can be on the right while the dialysate withdrawal tube can be on the left in other embodiments of the invention. Each ribbon shown in FIG. 4A-4B has five pairs of these tubes and there are five ribbons, so altogether there are 25 pairs of tubes. Each pair of tubes covers an area of about 2 mm×0.2 mm, and the wall 422 separating the delivery and removal tubes 411 and 412 of each pixel 410 has an opening that is G=0.3 mm tall. These tubes are smaller than conventional microdialysis tubes, which allows probing specific groups of cells, for example individual neurons in a brain slice. This is advantageous for identifying the secretomic signals associated with neuronal activation, differentiation, or response to toxins. The volume of dialysate to be detected with serial readouts in this embodiment is approximately 200 nanoliters, well within the detection range of on-line mass spectrometers.

The approach presented by this invention differs from the air-sampling mass spectrometry approaches discussed above. According to the invention, the approach has real-time pixels collecting the dialysate continuously with serial readout. However, the air-sampling mass spectrometry approaches have one collection probe moving around relative to the sample, which allows the analyte to diffuse away when the collection tube is not on top of the recording location. In addition, the approach allows for optimal transfer of dialysate across the semipermeable barrier and accumulation of dialysate for subsequent analysis without loss of analyte on the sample-side of the membrane, or reduction of collection efficiency because of the accumulation of analyte within the probe.

One aspect of the invention also provides a system for microdialysis imaging and regional fluidic delivery and control for dialyzing/retrodialyzing/culturing/controlling/analyzing the living bio-object. The living bio-object includes cells, tissues, or an organ of a living subject.

The system in one embodiment shown in FIG. 5 includes a microdialysis imager 501 including a imaging head having N pixels aligned in a pixel array 520 for monitoring a state of a living bio-object that is in fluidic communication with the pixel array 520, N being a positive integer greater than one. In this exemplary embodiment shown in FIG. 5, N=25. One exemplary embodiment of the imaging head is shown in FIGS. 4A-4B, where N=25 as well. In certain embodiments, N can be 10, 50, 100, etc.

The system also has a fluidic module 510 coupled to the microdialysis imager 501 for delivering a fluidic substance to and collecting effluent from the living bio-object. The fluidic module 510 includes a fluidic network having a plurality of valves, a plurality of fluidic channels 512 in fluidic communication with the plurality of valves and one or more pumps coupled to corresponding fluidic channels, required to control the delivery and collection of perfusate and dialysate, respectively, which are stored within or adjacent to the module (not shown). The fluidic module 510 also includes a microcontroller coupled to the fluidic network for individually controlling the plurality of valves and the one or more pumps of the fluidic network as so to operably and selectively deliver the fluidic substance to and continuously collect the effluent from the living bio-object responsive to the delivered fluidic substance via each pixel of the pixel array in real time.

In certain embodiments, the implementation of these valves is in accordance with inventors' earlier invention for a normally closed microfluidic valve [1], which is incorporated herein by reference in its entirety, and derivatives thereafter, including 25- and 100-port valves. In one embodiment, each valve is a rotary planar valve (RPV), and each pump is a rotary planar peristaltic micropump (RPPM). It should be appreciated that any other types of valves and pumps can also be utilized to practice the invention. In this embodiment, the dialysate is delivered to a mass spectrometer or other chemical analyzer (not shown). This fluidic module 510 is connected by a series of push-pull microfluidic channels 512 to the input and output of each of twenty-five recessed pixels 550. The semipermeable dialysis membrane 521 seals the top of the pixel array 520 to create an imaging head that contains the pixels array 520 that is inverted as compared to the ones shown in FIGS. 1A-1D, 2A-2B, and 3A-3C. In this inverted geometry, the cells 543 can be grown directly on the microdialysis membrane 521, or the tissue slice 543 can be placed on the membrane 543, with both then covered with a layer of cell culture or perfusion media 521. In certain embodiments, hundred-port valves support a 10×10 pixel array. In certain embodiments, the semipermeable membrane is made of polyarylonitrile, AN69, cuprophane, polycarbonate, polyamide, polysufone, and polyarylethersulfone.

In one embodiment, the fluidic module 510 is configured such that the fluidic substance delivered to the living bio-object is identical in each pixel 550 of the pixel array 520, or different in different pixels 550 of the pixel array 520. In one embodiment, the fluidic substance contains one or more fluids with a concentration of each fluid controllable in real time. In one embodiment, the fluidic substance has a one-dimensional or two-dimensional concentration gradient distribution across the pixel array 520. In one embodiment, the fluidic substance contains perfusate or drugs, transcription factors, nutrients, toxins, or other endogenous and exogenous chemical species, and the effluent contains dialysate, waste, signaling molecules, or drug or toxin metabolites from the living bio-object.

FIG. 6A show schematically a system for microdialysis imaging and regional chemical delivery and control according to another embodiment of the invention, where the fluidic module includes a delivery control unit 610 disposed on one side of the microdialysis imager 601/602 (pixel array 620) and a collection control unit 630 disposed on the other side of the microdialysis imager 601/602 (pixel array 620). The delivery control unit 610, the pixel array 620 and the collection control unit 630 are in fluidic communication with a number of push-pull microfluidic channels 612, so that the input and output of each pixel of the pixel array 620 are operably controllable by the delivery control unit 610 and/or the collection control unit 630. In certain embodiments, the delivery control unit 610 includes a 25-channel fluidic controller 610 for perfusate and localized retrodialysate delivery while the collection control unit 630 includes a 25-channel fluidic controller 630 for dialysate collection and direction to a mass spectrometer or other analytical instruments. In another embodiment, the fluidic controllers have 100 channels.

FIG. 6B shows schematically a close-up cross-section of how a single pixel 650 in the pixel array 620 is fabricated according to one embodiment of the invention, with standard soft-lithography techniques. Multiple pixels are adjacent to each other, sharing common walls 653 that define the pixel volume 651 beneath the semipermeable membrane 621 and support dialysate exchange 652 within the pixel 650.

Figure 6D:
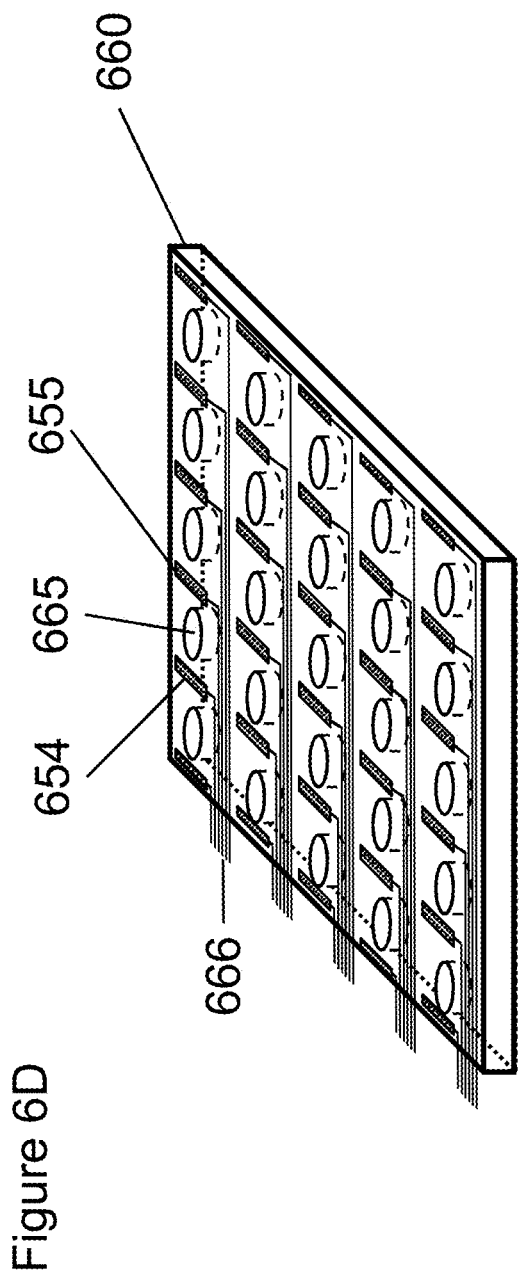
Figure 6E:
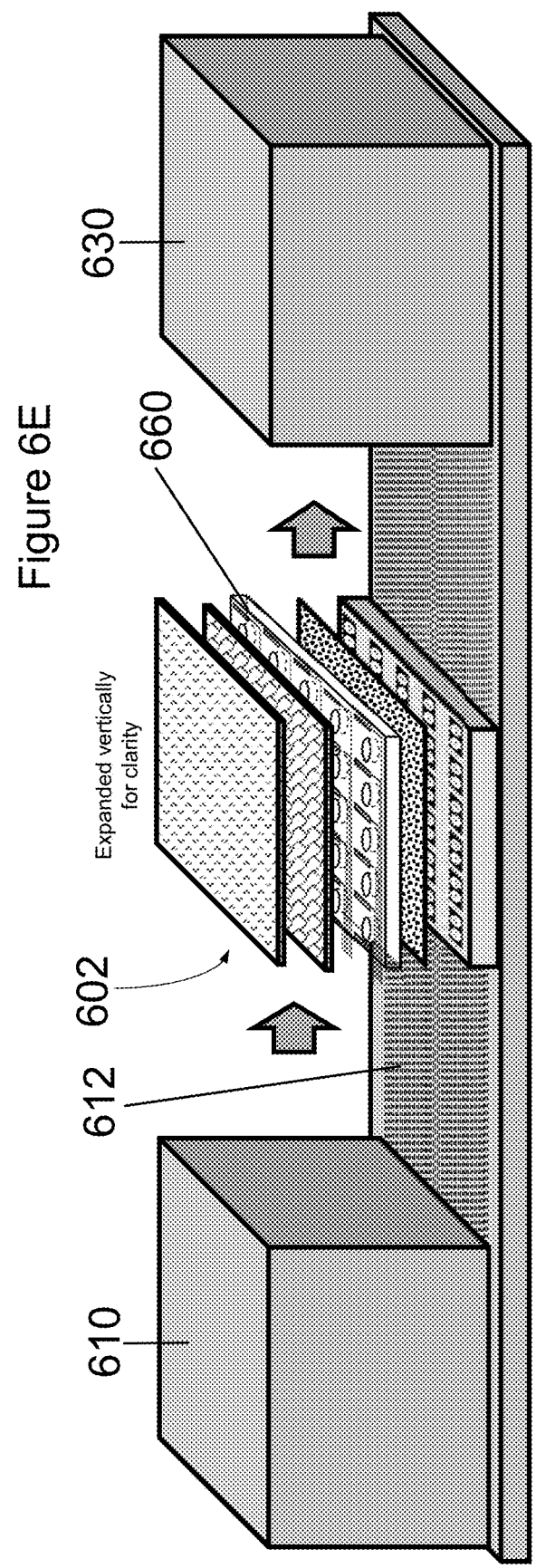

In certain embodiments, a microelectrode array (MEA) is superimposed on the semipermeable dialysis membrane 621, with a pair of electrodes 654 and 655, as shown in FIG. 6C, detecting the electrical activity of cells in the immediate vicinity of the recording microdialysis pixel. In some embodiments, the MEA is provided as a separate layer (e.g., a substrate) 660 above the semipermeable membrane 621, as shown in FIGS. 6D and 6E, where the substrate 660 of the MEA has through holes 665 to allow communication with the underlying pixel 650 and electrodes 645 and 655, for example, connected to appropriate detection electronics by thin-film leads 666.

It is extremely important to recognize that the input control valves of the channel fluidic control unit (or dialysate delivery unit) 610 shown in FIG. 6A allow a different cocktail to be retrodialyzed into each pixel 650. In certain embodiments, a multi-well microformulator disclosed in U.S. Pat. No. 10,023,832 by the inventors, which is incorporated herein by reference in its entirety, is used to control the concentration in each of the imaging pixels. This includes the generation of one- and two-dimensional spatial gradients 690 that are imposed upon the cells being microdialyzed, as shown in FIG. 6A. In this case, the dialysate delivery unit 610 is effectively a microformulator, and what is unique beyond the microformulator application is that the output of the delivery side of the microformulator 610, instead of being delivered to an open well, is delivering microdialysate to a probe with semipermeable membrane to dialyze cells or tissues outside of the probe, which is then collected by the equivalent collection side of a microformulator 630 to be passed on to one or more chemical analysis units. In addition, the microformulator as previously described has tubes that fit into open wells whose fluid volume can change over time, and the diameter of the tubes, their wall thickness, and the walls between the wells places a lower limit on the size of the pixels. According to the invention, the tubes that connect the valve to the sample form the pixels in a closed, fluidic system.

Another aspect of the invention provides a method for microdialysis imaging and regional fluidic delivery and control for dialyzing/retrodialyzing/culturing/controlling/analyzing the living bio-object. The living bio-object includes cells, tissues, or an organ of a living subject.

In one embodiment, the method includes providing a microdialysis imager and a fluidic network, where the microdialysis imager includes a imaging head having N pixels aligned in a pixel array for monitoring a state of the living bio-object that is in fluidic communication with the pixel array, N being a positive integer greater than one, and where the fluidic network is coupled to the microdialysis imager and a plurality of fluids and includes a plurality of valves, a plurality of fluidic channels in fluidic communication with the plurality of valves, and one or more pumps coupled to corresponding fluidic channels; and individually controlling the plurality of valves and the one or more pumps of the fluidic network to operably and selectively deliver a fluidic substance to and continuously collect the effluent from the living bio-object responsive to the delivered fluidic substance via each pixel of the pixel array in real time, where the fluidic substance contains one or more of the plurality of fluids.

In one embodiment, the controlling step includes controlling the fluidic substance delivered to the living bio-object to be identical in each pixel of the pixel array, or to be different in different pixels of the pixel array.

In one embodiment, the controlling step includes controlling the fluidic substance to have a concentration of each fluid being constant or varying with time.

In one embodiment, the controlling step includes controlling the fluidic substance to have a one-dimensional or two-dimensional concentration gradient distribution across the pixel array.

Key features of this invention that make it different from a simple parallelization of the approach, as would be suggested in FIGS. 3A-3C, is that the loading of the dialysate and its withdrawal are performed as a sequence of individual steps. At issue is the efficiency of dialysis across a semipermeable membrane, which decreases as the concentration of the collected analyte increases with time. The current invention avoids this by regularly or continuously providing fresh media to each pixel, and storing the higher-concentration media in the channel beyond the dialysis chamber to accumulate a sufficient volume of media for subsequent analysis. This process of dialysate refreshment and storage from multiple pixels is not possible in any simple, parallel system.

Figure 7A:
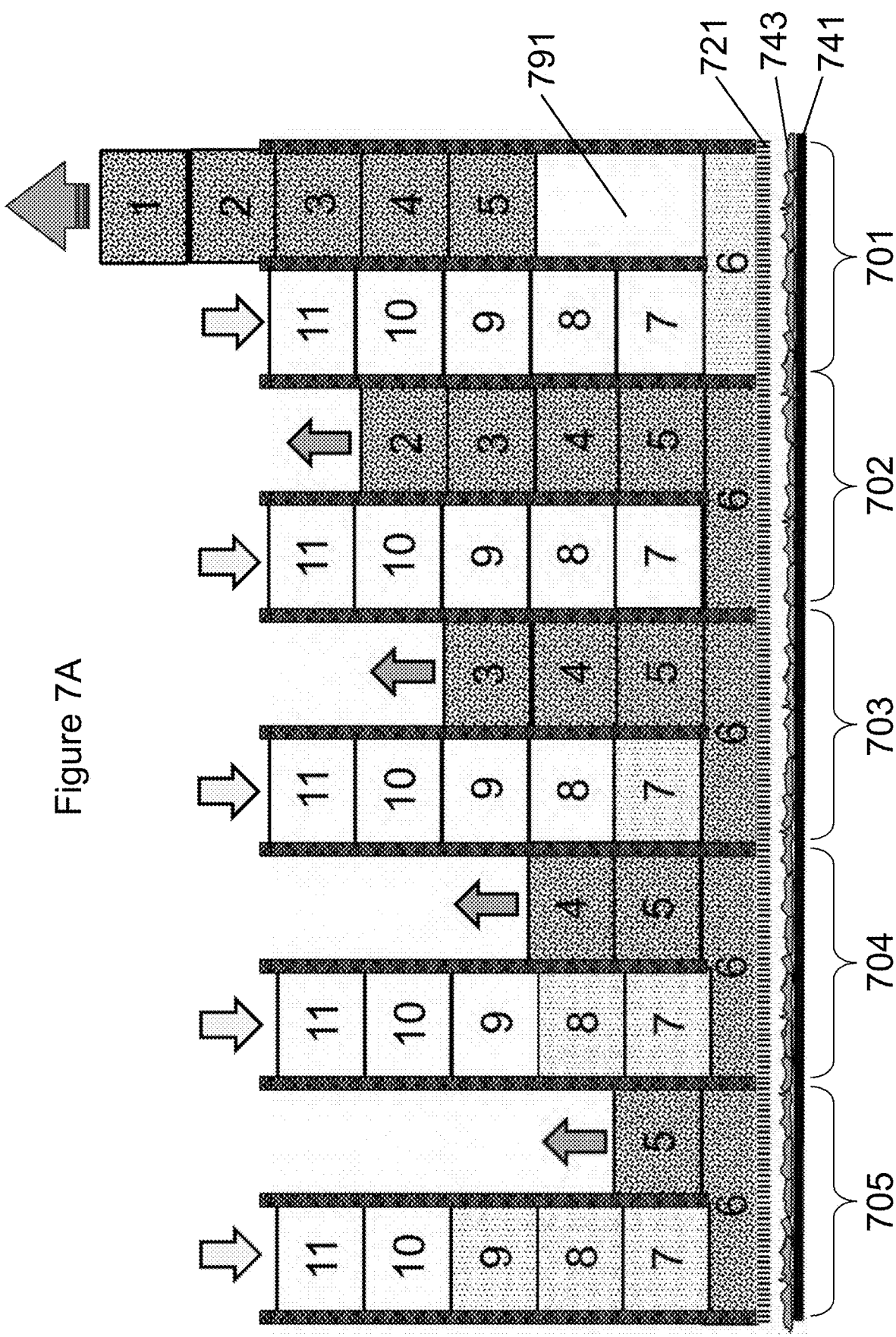
FIGS. 7A-7B show schematically a process for the sequential loading of each pixel with aliquots of dialysate and the subsequent transfer of multiple aliquots to a chemical analyzer to enable both microdialysis imaging and regional fluidic delivery and control for dialyzing/retrodialyzing/culturing/controlling/analyzing the living bio-object according to one embodiment of the invention.

Another key feature of this invention is that it provides parallel pixel loading, parallel pixel collection, and then serial pixel readout. This process allows us to accumulate in the collection tube/channel or a collection reservoir the volume of dialysate that is required, for example, for mass spectrometric analysis without requiring very large pixels. FIG. 7A shows a schematic representation of the first steps in the process according to one embodiment of the invention. In the exemplary embodiment, a pixel head including a five-pixel array with dual-channel pixels 701, 702, 703, 704, and 705 is provided. The cells/tissue slice 743 supported by the planar surface 741 is being microdialyzed through the semipermeable membrane 721. For the illustration of the process, a "clock step" is considered as the time interval required to add a bolus or aliquot of dialysate media to each pixel in the pixel array. In the first time step, only the pixel 701 is loaded. In the second time step, a bolus of dialysate is delivered to both the pixels 701 and 702. In the third time step, a bolus is added to each of the pixels 701, 702 and 703. By the fifth time step, all the five pixels 701-705 have been loaded. But as a fresh bolus of dialysate is added to each pixel in each time step, the previously occupying one, if present, is displaced along the collection channel. Hence, each "clock step" comprises five "pixel steps".

In this example, it is assumed that five clock steps are sufficient to deliver the volume required for analysis by the mass spectrometer or other instrument. In the fifth clock step, in this example, the volume of fluid 791 delivered to the pixel 701 is sufficient to drive the first five aliquots (Nos. 1-5) of fluid out of the pixel 701 collection chamber into the analysis system (e.g., the analyzer 270 shown in FIG. 2A). The next aliquot (No. 6) is delivered to the pixel 701 to restart the dialysis process that will be completed at the end of four more clock steps, and an aliquot is delivered to the other four pixels during the five pixel steps that constitute a single clock step. Because of the staggered loading of the pixels, there is, at the beginning of the next cycle, one aliquot (No. 6) in the pixel 701, five aliquots (Nos. 2-6) in the pixel 702, four aliquots (Nos. 3-6) in the pixel 703, three aliquots (Nos. 4-6) in the pixel 704, and two aliquots (Nos. 5-6) in the pixel 705.

Figure 7B:
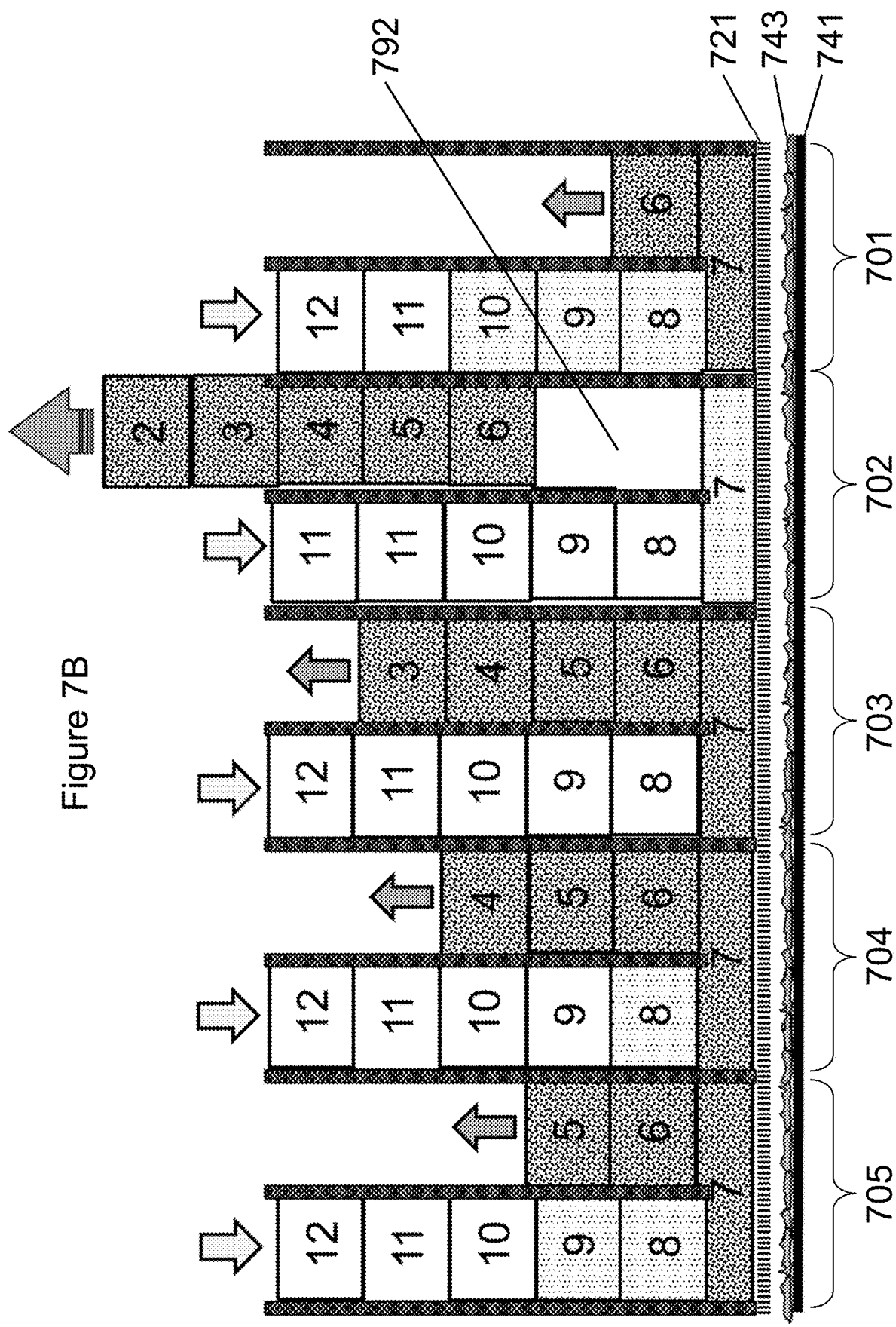

FIG. 7B shows the next clock step—aliquots No. 2 through No. 6 are being ejected from the pixel 702 by the large aliquot 792, and all the other pixels 701, 703, 704 and 705 receive the standard, smaller aliquot.

Figure 8A:
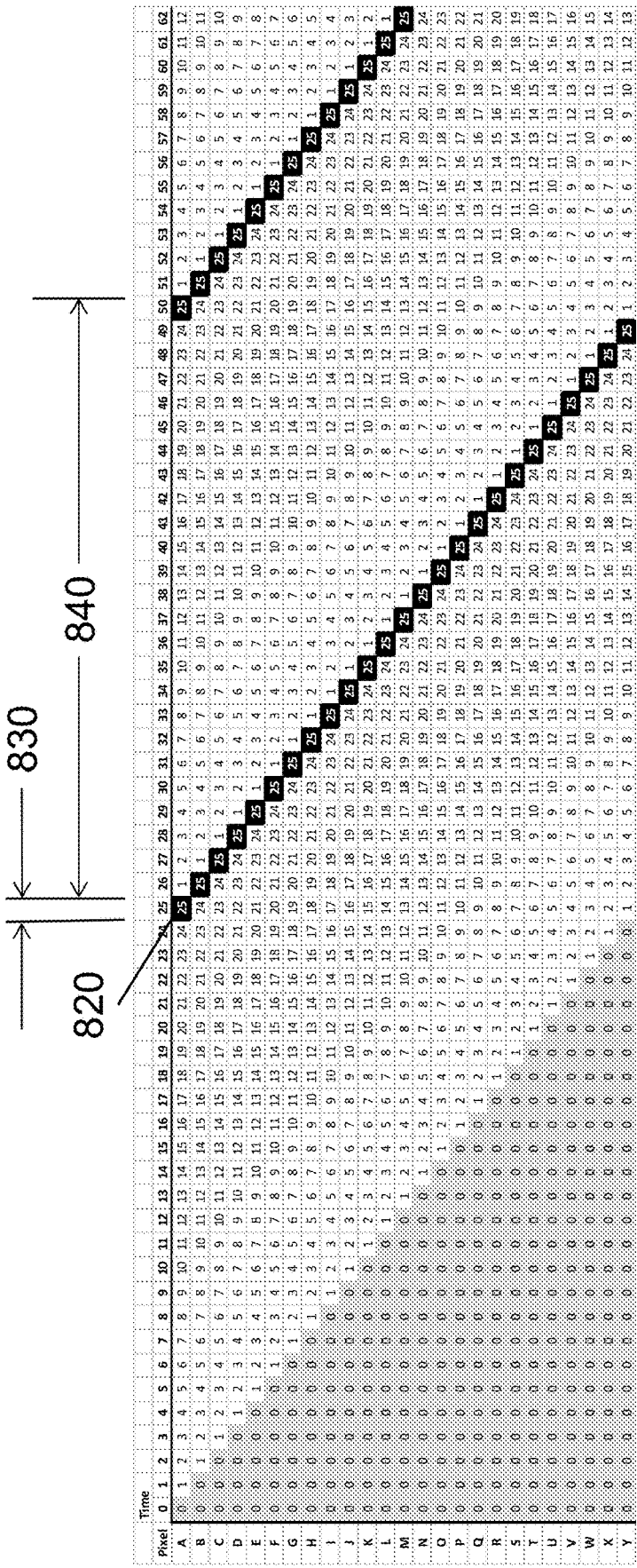

FIG. 8A shows schematically a representation of the loading process for a twenty-five pixel array according to one embodiment of the invention. The pixels are labeled A through Y on the left, and the time steps from 1 through 62 are labeled on the top. The number shown in each square represents the number of aliquots filled in each pixel in a respective time step. For this example, it is assumed that 25 aliquots, each of volume 1.0, are required to fill a pixel for transfer to the chemical analyzer that is driven by the fluidic module 510 shown in FIG. 5. The lower left corner (grey boxes with zeros) 810 represents the staggered initial loading of each pixel. By time step 25, pixel A has been filled and is ready for off-loading to the chemical analyzer, and that square 820 is filled with black with the number of 25. It is assumed that the time required to process one pixel with the chemical analyzer is equal to one clock step 830.

During the next clock step (step 26), pixel B is off-loaded. In each clock step, every pixel receives a fresh aliquot of media to ensure continuous, high-efficiency dialysis, and after 25 clock steps (840), the cycle returns to off-loading of pixel A.

In one embodiment, it is feasible to run 100 nL per minute into a Waters Corporation ultra performance liquid chromatography ion mobility mass spectrometer (UPLC-IM-MS) to obtain data with 10 minute time resolution, as already demonstrated by the inventors [10, 11]. A 25-pixel image acquired with this system would then require 4.2 hours. Obviously, there is a trade-off between depth of molecular coverage, sample volume, and spatio-temporal resolution. A faster mass spectrometer would process samples more quickly and hence operate at a shorter imaging interval. It is important to recognize that the UPLC used by the inventors [11] was used for desalting of the media, and it could also be used for timed, gradient elution of chemical species with different affinities to the UPLC column. The key point is that the minimum duration of whatever chemical analysis is performed sets the minimum step size 820 in FIG. 7B In another embodiment, an Agilent Rapid-Fire solid-phase extraction (SPE) system is used instead of a UPLC MS system for both desalting and species separation, a single sample is analyzed in 10 seconds. That, in this example, allows capture of a complete image every 4.2 minutes (10×25/60). If additional SPE separation and mass spectrometer modes are used, the analysis time is extended to 40 seconds per pixel to obtain positive- and negative-mode MS data with hydrophobic and hydrophilic SPE cartridges, for an imaging time of 17 minutes. It is important to appreciate that the incremental loading of each pixel, as shown in FIG. 8A, ensures that every pixel is dialyzed efficiently during the entire interval 840 required to capture an entire image. Because of the temporal integration of dialysate over that interval and the spatial integration of closely spaced pixels, there are no risk of either spatial or temporal aliasing. Features in the bio-object that occur faster than the image capture interval 840 or with a higher spatial resolution will be averaged out. There will be a skew in in the image determined by the order by which the pixels are sampled, in that some of the pixels will be measured early in a clock step than others, but this will be done in a repeatable manner.

In addition, were a faster "frame rate" required for the imaging, the aliquot volume could be increased to, for example 2.5 from 1.0 "volume units." The time to capture a complete image would be 10 clock steps, the reciprocal of which is the imaging frame rate. By step 10, pixel A has been filled and is ready for off-loading to the chemical analyzer, and that square is filled with black with the number of 25. After 10 clock steps (850), the cycle returns to off-loading of pixel A. However, if 25 pixels are still sampled, as shown in FIG. 8B, for all times greater than 19 it will be necessary to analyze two or more samples with each clock step, possibly violating the speed limit set by the chemical analyzer.

Figures 8B, 8C:
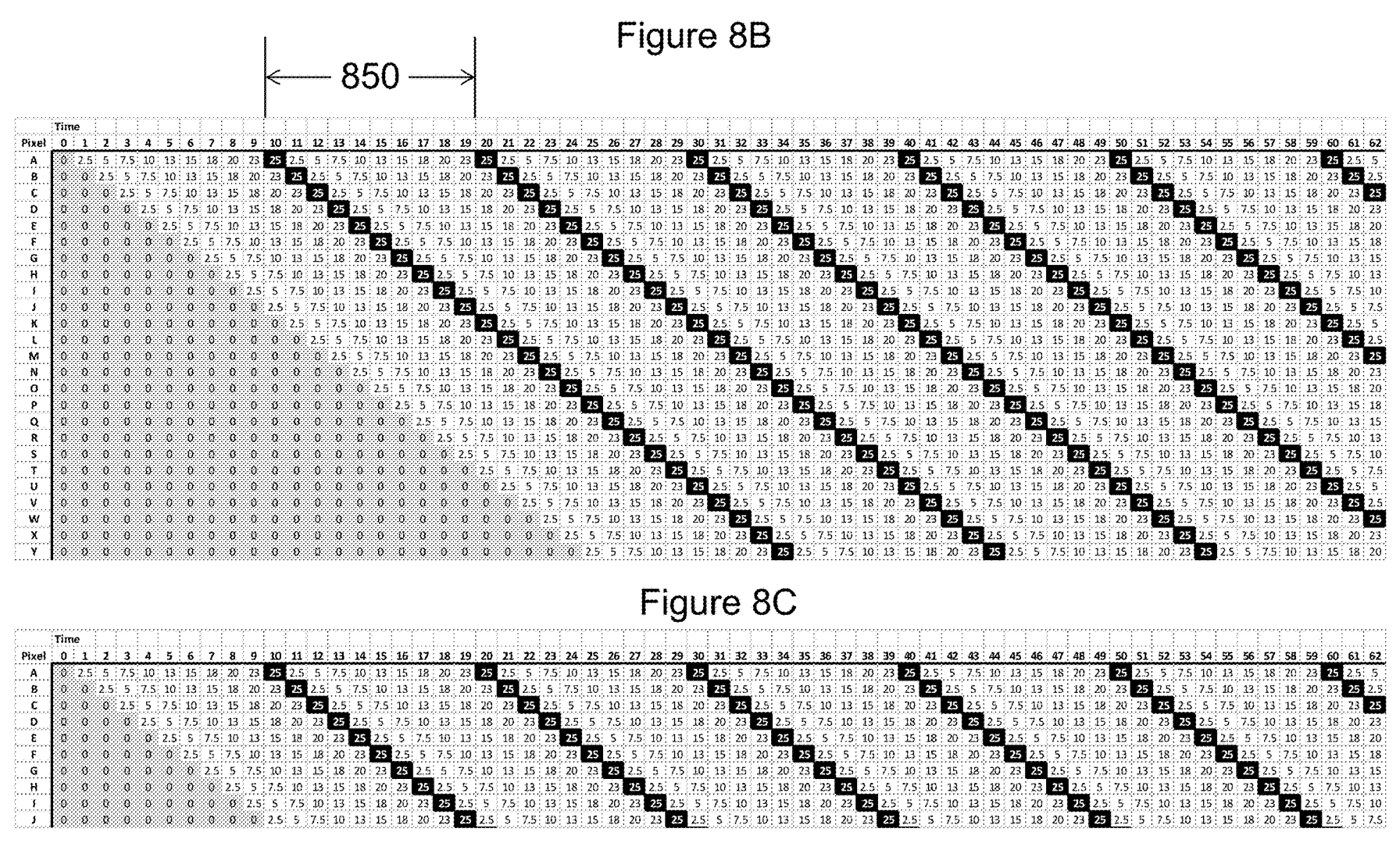

One alternative, shown in FIG. 8C, is to limit the number of pixels to be analyzed, in this specific exemplary case to a 10-pixel array. Accordingly, the frame interval of the microdialysis camera is the product of the speed with which a dialysate sample is analyzed times the number of pixels being imaged. The sensitivity of the detection is determined in part by the volume of fluid that is analyzed in each clock step. The ability to extract the maximum amount of analyte is determined in part by the number of clock steps allocated to filling each pixel and the storage volume in the line or a reservoir between the pixel and the downstream analyzer.

Therefore, for an N-pixel array, in a full clock step a single aliquot of perfusate is delivered to each pixel in N sub-cycles (pixel steps). In the serial loading, at any time, each of the pixels contains a different number of aliquots so that only one pixel is ready for analysis each clock step. After the Nth aliquot is delivered to a pixel and allowed to dialyze the cells/tissues, the N aliquots are then transferred to the chemical analyzer, and a single, fresh, aliquot is left in that pixel to start a new full cycle. During N full cycles, each pixel will be transferred the mass spectrometer as a single bolus containing N aliquots. The semipermeable membrane sees fresh perfusate each sub-cycle to optimize dialysis, and the dialysate is accumulated between transfers to the mass spectrometer or other chemical analyzer.

In certain embodiments of the invention, it may be useful to provide demarcation between the bolus of fluid that is delivered to the chemical analyzer from different pixels. This can be readily accomplished by injecting, for example, a small bubble of air between samples obtained from the source of pressurized air or other gas 933 connected to one of the ports of the 101-channel output collector valve 932 (If desired valve 932 could be a 102-channel valve, with the $102^{nd}$ port being connected to a flush vial as was done for valve 912). A bubble detector 945 can then be used to detect the end of one sample and the beginning of another. A similar approach could be accomplished with a bolus of oil or other fluid that is immiscible with the dialysate. Bubble detectors could be placed at more than one location in the system if desired. If necessary to avoid sample-sample crosstalk, the separator between two samples could be two or more bubbles or oil drops separated by a blank aqueous bolus. The pumps, valves, and tubing can be selected for or treated to cause all surfaces to be highly hydrophobic to minimize both the retention of analyte in the system and the drag experienced by the air bubbles that separate each bolus. The normally closed rotary planar valves [1] are all designed to have a flush port so that the common channel of each valve can be flushed with pure dialysate, a buffer, water, or air between passage of each sample bolus. The system can be rinsed between injections as many times as is needed to reduce analyte from the previous bolus to below the limit of detectability. Once the rinses are complete, the next bolus can be run.

Figure 9:
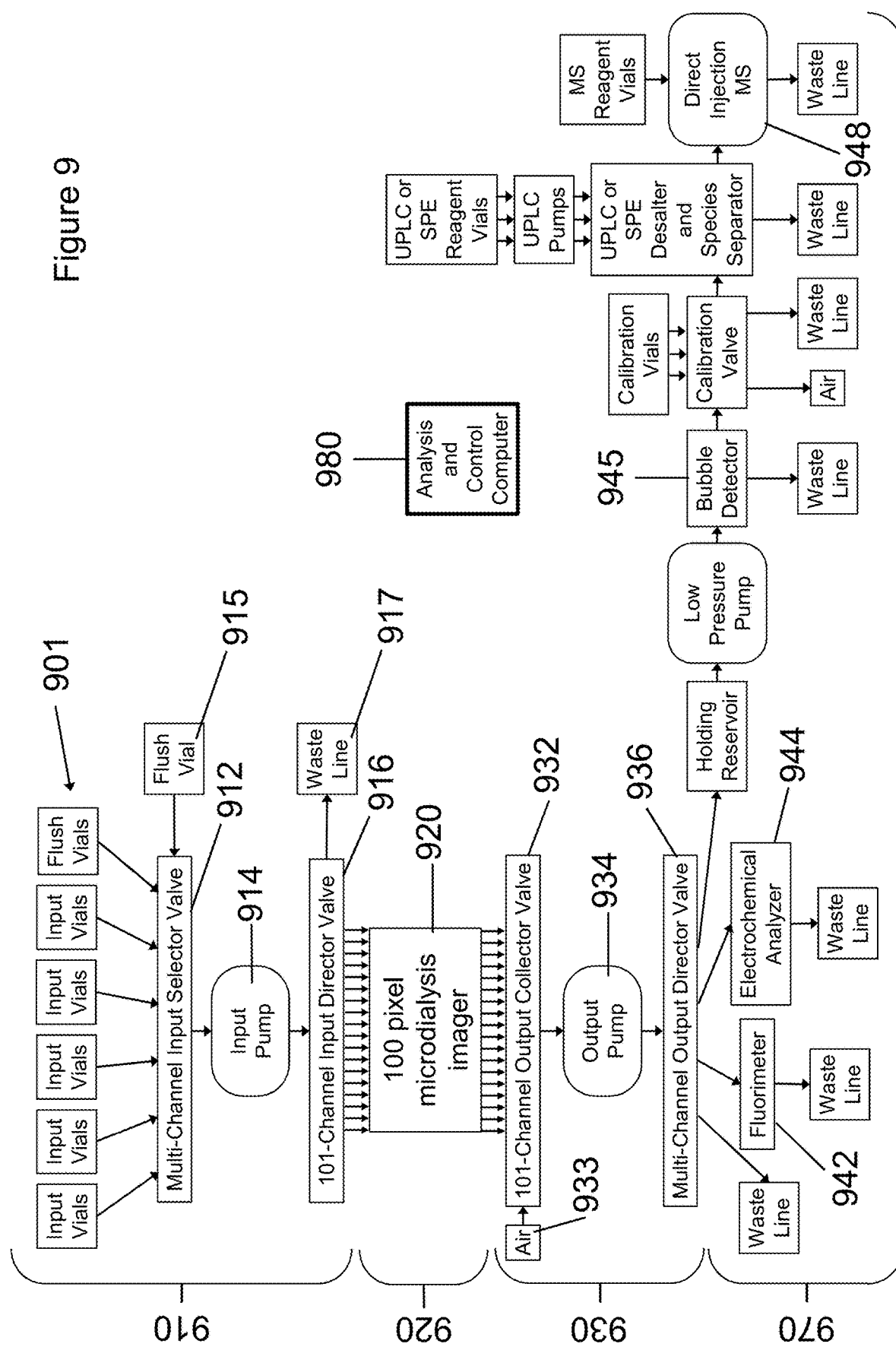
FIG. 9 shows schematically a system for microdialysis imaging and regional fluidic delivery and control for dialyzing/retrodialyzing/culturing/controlling/analyzing the living bio-object according to one embodiment of the invention.

FIG. 9 illustrates schematically a system for microdialysis imaging and regional fluidic delivery and control for dialyzing/retrodialyzing/culturing/controlling/analyzing the living bio-object according to one embodiment of the invention, which includes a reagent/dialysate delivery control unit 910, the microdialysis imager 920, and a dialysate/analyte collection control unit 930.

In the exemplary embodiment, the delivery control unit includes at least one multi-channel input selector valve 912 coupled to a plurality of input ports 901 that operably provides a plurality of fluids, at least one input pump 914 coupled to the at least one multi-channel input selector valve 912, and at least one multi-channel input director valve 916 coupled to the at least one input pump 914. The collection control unit 930 includes at least one multi-channel output collector valve 932, at least one output pump 934 coupled to the at least one multi-channel output collector valve 932 and at least one multi-channel output director valve 936. The microdialysis imager 920 is coupled between the at least one multi-channel input director valve 916 of the delivery control unit 910 and the at least one multi-channel output collector valve 932 of the collection control unit 930.

In order to back-flush the multi-channel input selector valve 912, the last input on the valve is connected to a flush vial 917 filled with flushing media, such as distilled water or plain dialysate. The pump 914 then directs that to the 101-channel input director valve 916, whose last port is the waste line 917. This ensures that both valves 912 and 916 and pump 914 are flushed of whatever chemical that would be delivered to one pixel but not the next one to which fluid would be added.

In certain embodiments, the at least one multi-channel input selector valve 912 is adapted for providing the fluidic substance containing one or more of the plurality of fluids selectively from the plurality of input ports 901. The at least one multi-channel input director valve 916 is adapted for directing/delivering the fluidic substance to desired pixels in the pixel array of the microdialysis imager 920. The at least one multi-channel output collector valve 932 is adapted for collecting the effluent from the living bio-object responsive to the delivered fluidic substance via each pixel of the pixel array in real time, which, in turn, is directed by the at least one multi-channel output director valve 936 to an analyzer (e.g., 970) for analysis.

In addition, the system also includes an analyzer unit 970 coupled to the at least one multi-channel output director valve 936 of the collection control unit 930. In one embodiment, the analyzer unit includes a fluorimeter 942, an electrochemical analyzer 944, a mass spectrometer 948, other chemical detectors (not shown, including a capillary electrophoresis detector, a liquid chromatography detector, or a radiation detector, an impedance/conductance analyzer, etc., or a combination of one or more thereof.

Furthermore, the system includes an analysis and control computer 980 that is electrically coupled to the pumps, valves, sensors, and detectors by wired or wireless connections. As shown, the pumps and valves are connected to a variety of reservoirs, fluidic and air lines, and other components, all which operate in the coordinated fashion described above.

Closed-loop control system: The system as described above can be used for simultaneous dialysis of living cells and tissues to detect the chemical compounds absorbed from and released to the media that bathes the cells and tissues, and retrodialysis of those same cells and tissue to deliver compounds that will alter the metabolism and signaling of these cells or tissues. The ability to simultaneously sense and control cell/tissue state is critical for the closed-loop control of biology.

Because of the total spatial control of the retrodialysis process, a variety of gradients and other spatial patterns of nutrients, drugs, toxins, metabolites, and signaling molecules can be delivered to the biological sample under study. This can, for example, be used to recapitulate the spatiotemporal gradients in signaling molecules that drive the differential development of cells in complex tissues, for example the developing brain. Through those influences combined, the cells are differentiated into one or more target types of cells (for example, neuronal stem cells may be differentiated into various kinds of mature neurons). The system is flexible enough to accommodate having many different kinds of cells present at both the beginning and end of its use; this is important if the user is trying to recapitulate the development of a tissue, rather than just produce many cells of one type.

Practical Applications:

In vivo microdialysis is typically performed on experimental animals. There are cases where in vivo microdialysis is performed to help treat epileptic patients [12]. However, these inter-operative recording do not shed light on the signaling involved in neural differentiation during brain development, which is largely complete by the time of recordings recordings might be possible intraoperatively in humans.

Traditional in vitro microdialysis involves harvesting neural tissue, such as a brain slice, from an organism, for example from a rat or mouse, stimulating it, and then observing the microdialysis signal. Similar to the in vivo microdialysis, such experiments performed with human brains would be constrained due to ethical concerns and the difficulty in acquiring functional slices of living human brain tissue. Although it might possible to perform such an experiment, it is difficult to do so and could raise ethical issues. However, point recordings or scanned point recordings provide an incomplete representation of the spatiotemporal processes in the developing and mature brain, both in health and disease. The microdialysis imager of the invention overcomes these limitations by enabling microdialysis measurements on human-derived cells grown in vitro as a brain-on-a-chip [45-47]. It is ethical to use brain organ-chips and organoids, which have the spatial organization necessary for an accurate representation of neural activity. The microdialysis imager can therefore be used to study how the spatial properties of tissues affect the pharmacokinetic and pharmacodynamic (PK-PD) properties of drugs.

The microdialysis imager provides important information to discern the mechanisms active during cellular differentiation, in that it can be used to detect cellular proteomic (large biomolecule) and metabolomic (small molecule) secretions without destroying the cells under study, as would be required to determine the levels of gene transcription, protein expression, and metabolite generation (the cellular multi-ome) within the cells. For researchers to infer the cellular multi-ome from just the cellular secretome, they need to develop an increasingly refined mathematical and/or computational framework for mapping cellular state space. State-of-the-art machine learning techniques can be used to empirically connect non-invasive secretomics data as acquired by the microdialysis imager to destructive multi-omics data (a black box approach), and mechanistic models will be created in parallel using a combination of canonical knowledge and efficient network reconstruction algorithms (gray box and white box approaches). Together, these models will be used to develop a model-based control framework which is robust to errors, noise, and cell type. This framework will be implemented as an automated, closed-loop control system to efficiently control and direct cellular states using the microfluidic retrodialysis delivery system and the microdialysis imager.

In addition, the microdialysis imager allows the ability to measure for in vitro models of brain tissue the spatial variations in the secretome of neuronal cells (neurotransmitters and metabolites) that result from the activity of an individual cell and the signaling from neighboring cells. It is difficult to obtain a microdialysis time series for human neural tissues due to ethical concerns, and animal analogues are insufficient for recapitulating the complexity of human neurophysiology. Although there are similarities between human neural tissues and animal neural tissues, the human brains are more complex than animal brains. Although it is ethical in animals, in vivo microdialysis unethical for studying human development; in vivo microdialysis involves monitoring the secreted factors of cells in the brain while the organism is still alive. This setup involves inserting a microdialysis probe directly into the brain region of interest. Although these experiments can be performed with animals, it is unethical to perform such experiments with humans due to the potential irreversible and life-threatening harm such a procedure can cause if done improperly. Hence a system that can perform brain microdialysis in a three-dimensional in vitro model of human brain tissue would have great value.

In vivo microdialysis is also utilized for secretomic biomarker collection and drug delivery. There is interest in using this technique in application to study cancer [48] and wound healing [49, 50]. The microdialysis imaging head can potentially bring greater resolution to both of these applications to resolve the dynamics of the cancer tumor microenvironment and wound healing secretions. The use of the microdialysis imager to study human and animal tissues and in vitro organ-on-chip models could advance the study of the complex dynamics of wound healing and cancer natively and under perturbations such as drugs, mutations, and environmental influences. If the technology is further refined, methods could be developed for using the microdialysis imager in the operating room for spatially probing the microenvironment of a patient's tumors, applying a spatially-resolved drug treatment to the tumor microenvironment, and specialized wound treatment.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

REFERENCES LIST

[1]. Block III, F. E., et al. (2017). Normally closed microvalve and applications of the same. U.S. Pat. No. 9,618,129, Vanderbilt University.

[2]. Caldwell, R. L. and R. M. Caprioli (2005). "Tissue profiling by mass spectrometry—A review of methodology and applications." Molecular and Cellular Proteomics 4(4): 394-401.

[3]. Calligaris, D., et al. (2013). "Mass spectrometry imaging as a tool for surgical decision-making." Journal of Mass Spectrometry 48(11): 1178-1187.

[4]. Chaurand, P., et al. (2002). "Imaging mass spectrometry: a new tool to investigate the spatial organization of peptides and proteins in mammalian tissue sections." Current Opinion in Chemical Biology 6(5): 676-681.

[5]. Comi, T. J., et al. (2017). "MALDI MS Guided Liquid Microjunction Extraction for Capillary Electrophoresis-Electrospray Ionization MS Analysis of Single Pancreatic Islet Cells." Analytical Chemistry 89(14): 7765-7772.

[6]. de Macedo, C. E. A., et al. (2016). Brain Microdialysis. Rodent Model as Tools in Ethical Biomedical Research. M. L. Andersen and S. Tufik. Cham, Springer International Publishing: 217-233.

[7]. Dhunna, M. (2015). Desorption Electrospray Ionization Mass Spectrometry Imaging: Instrumentation, Optimization and Capabilities. Chemistry and Biochemistry. Provo, Utah, Brigham Young University. MS.

[8]. Dunham, S. J. B., et al. (2017). "Mass Spectrometry Imaging of Complex Microbial Communities." Accounts of Chemical Research 50(1): 96-104.

[9]. Eberlin, L. S., et al. (2011). "Desorption electrospray ionization mass spectrometry for lipid characterization and biological tissue imaging." Biochimica Et Biophysica Acta-Molecular and Cell Biology of Lipids 1811(11): 946-960.

[10]. Enders, J. R., et al. (2010). "Towards monitoring real-time cellular response using an integrated microfluidics-MALDI/NESI-ion mobility-mass spectrometry platform." IET Systems Biology 4(6): 416-427.

[11]. Enders, J. R., et al. (2012). "A Dual-Column Solid Phase Extraction Strategy for Online Collection and Preparation of Continuously Flowing Effluent Streams for Mass Spectrometry." Analytical Chemistry 84(20): 8467-8474.

[12]. Fried, I., et al. (1999). "Cerebral microdialysis combined with single-neuron and electroencephalographic recording in neurosurgical patients—Technical note." Journal of Neurosurgery 91(4): 697-705.

[13]. Gill, E. L., et al. (2017). "Monitoring Dopamine ex Vivo during Electrical Stimulation Using Liquid-Microjunction Surface Sampling." Analytical Chemistry 89(24): 13658-13665.

[14]. Girod, M., et al. (2010). "Desorption Electrospray Ionization Imaging Mass Spectrometry of Lipids in Rat Spinal Cord." Journal of the American Society for Mass Spectrometry 21(7): 1177-1189.

[15]. Griffiths, R. L., et al. (2018). "Ambient surface mass spectrometry-ion mobility spectrometry of intact proteins." Current Opinion in Chemical Biology 42: 67-75.

[16]. Griffiths, R. L., et al. (2017). "Raster-Mode Continuous-Flow Liquid Microjunction Mass Spectrometry Imaging of Proteins in Thin Tissue Sections." Analytical Chemistry 89(11): 5684-5688.

[17]. Ifa, D. R. and L. S. Eberlin (2016). "Ambient Ionization Mass Spectrometry for Cancer Diagnosis and Surgical Margin Evaluation." Clinical Chemistry 62(1): 111-123.

[18]. Kertesz, V., et al. (2005). "Automation of a surface sampling probe/electrospray mass spectrometry system." Analytical Chemistry 77(22): 7183-7189.

[19]. Kertesz, V. and G. J. Van Berke (2013). "Automated liquid microjunction surface sampling-HPLC-MS/MS analysis of drugs and metabolites in whole-body thin tissue sections." Bioanalysis 5(7): 819-826.

[20]. Kertesz, V. and G. J. Van Berkel (2010). "Fully automated liquid extraction-based surface sampling and ionization using a chip-based robotic nanoelectrospray platform." Journal of Mass Spectrometry 45(3): 252-260.

[21]. Kertesz, V. and G. J. Van Berkel (2010). "Liquid Microjunction Surface Sampling Coupled with High-Pressure Liquid Chromatography-Electrospray Ionization-Mass Spectrometry for Analysis of Drugs and Metabolites in Whole-Body Thin Tissue Sections." Analytical Chemistry 82(14): 5917-5921.

[22]. Kumara, P. M., et al. (2016). "Desorption Electrospray Ionization (DESI) Mass Spectrometric Imaging of the Distribution of Rohitukine in the Seedling of Dysoxylum binectariferum Hook. F." PloS One 11(6).

[23]. Lane, A. L., et al. (2009). "Desorption electrospray ionization mass spectrometry reveals surface-mediated antifungal chemical defense of a tropical seaweed." Proceedings of the National Academy of Sciences of the United States of America 106(18): 7314-7319.

[24]. LeDuc, P. R., et al. (2011). "How do control-based approaches enter into biology?" Annual Review of Biomedical Engineering 13: 369-396.

[25]. Lee, J. K., et al. (2016). "High-Resolution Live-Cell Imaging and Analysis by Laser Desorption/Ionization Droplet Delivery Mass Spectrometry." Analytical Chemistry 88(10): 5453-5461.

[26]. Lorenz, M., et al. (2013). "Laser microdissection and atmospheric pressure chemical ionization mass spectrometry coupled for multimodal imaging." Rapid Communications in Mass Spectrometry 27(13): 1429-1436.

[27]. MacVane, S. H., et al. (2014). "In vitro microdialysis membrane efficiency of broad-spectrum antibiotics in combination and alone." Clinical Pharmacology: Advances and Applications 6: 97-101.

[28]. Marasco, C. C., et al. (2015). "Real-time Cellular Exometabolome Analysis with a Microfluidic-mass Spectrometry Platform." PloS One 10(2).

[29]. Monge, M. E. and F. M. Fernandes (2014). An Introduction to Ambient Ionization Mass Spectrometry. Ambient Ionization Mass Spectrometry M. Domin and R. Cody: 1-22.

[30]. Nguyen, S. N., et al. (2017). "Constant-Distance Mode Nanospray Desorption Electrospray Ionization Mass Spectrometry Imaging of Biological Samples with Complex Topography." Analytical Chemistry 89(2): 1131-1137.

[31]. Norris, J. L., et al. (2003). "Mass spectrometry of intracellular and membrane proteins using cleavable detergents." Analytical Chemistry 75(23): 6642-6647.

[32]. Ovchinnikova, O. S., et al. (2013). "Laser Ablation Sampling of Materials Directly into the Formed Liquid Microjunction of a Continuous Flow Surface Sampling Probe/Electrospray Ionization Emitter for Mass Spectral Analysis and Imaging." Analytical Chemistry 85(21): 10211-10217.

[33]. Pan, N., et al. (2015). "Single-Cell MS and High-Spatial-Resolution MS Imaging Under Ambient Conditions Using a Novel Sampling Device." Lc Gc North America 33(6): 414-419.

[34]. Quanico, J., et al. (2017). "NanoLC-MS coupling of liquid microjunction microextraction for on-tissue proteomic analysis." Biochimica Et Biophysica Acta-Proteins and Proteomics 1865(7): 891-900.

[35]. Rao, W., et al. (2016). "Applications of the Single-probe: Mass Spectrometry Imaging and Single Cell Analysis under Ambient Conditions." Jove-Journal of Visualized Experiments(112).

[36]. Sinclair, I., et al. (2016). "Novel Acoustic Loading of a Mass Spectrometer: Toward Next-Generation High-Throughput MS Screening." Journal of Laboratory Automation 21(1): 19-26.

[37]. Svatos, A. (2010). "Mass spectrometric imaging of small molecules." Trends in Biotechnology 28(8): 425-434.

[38]. Van Berkel, G. J. and V. Kertesz (2009). "Application of a Liquid Extraction Based Sealing Surface Sampling Probe for Mass Spectrometric Analysis of Dried Blood Spots and Mouse Whole-Body Thin Tissue Sections." Analytical Chemistry 81(21): 9146-9152.

[39]. Van Berkel, G. J. and V. Kertesz (2013). "Continuous-flow liquid microjunction surface sampling probe connected on-line with high-performance liquid chromatography/mass spectrometry for spatially resolved analysis of small molecules and proteins." Rapid Communications in Mass Spectrometry 27(12): 1329-1334.

[40]. Van Berkel, G. J., et al. (2008). "Liquid microjunction surface sampling probe electrospray mass spectrometry for detection of drugs and metabolites in thin tissue sections." Journal of Mass Spectrometry 43(4): 500-508.

[41]. Wisztorski, M., et al. (2017). Droplet-Based Liquid Extraction for Spatially-Resolved Microproteomics Analysis of Tissue Sections. Imaging Mass Spectrometry: Methods and Protocols. L. M. Cole. New York, N.Y., Springer New York: 49-63.

[42]. Wu, C. P., et al. (2013). "Mass spectrometry imaging under ambient conditions." Mass Spectrometry Reviews 32(3): 218-243.

[43]. Zheng, Q. L. and H. Chen (2016). Development and Applications of Liquid Sample Desorption Electrospray Ionization Mass Spectrometry. Annual Review of Analytical Chemistry. P. W. Bohn and J. E. Pemberton. 9: 411-448.

[44]. Bradberry, C. W., et al. (1991). "In vitro Microdialysis: A novel technique for stimulated neurotransmitter release measurements." Journal of Neuroscience Methods 36(1): 85-90.

[45]. Brown, J. A., et al. (2016). Metabolic consequences of inflammatory disruption of the blood-brain barrier in an organ-on-chip model of the human neurovascular unit, Journal of Neuroinflammation 13:306.

[46]. Brown, J. A., et al. (2015). Recreating blood-brain barrier physiology and structure on chip: A novel neurovascular microfluidic bioreactor, Biomicrofluidics 9: 054124.

[47]. Brown, J. A., et al. (2014). Metabolic Consequences of Interleukin-6 Challenge in Developing Neurons and Astroglia. Journal of Neuroinflammation 11:183.

[48]. Brown, K. J. et al. The human secretome atlas initiative: Implications in health and disease conditions. Biochim. Biophys. Acta—Proteins Proteomics 1834, 2454-2461 (2013).

[49]. Förster, Y. et al. Microdialysis Sampling from Wound Fluids Enables Quantitative Assessment of Cytokines, Proteins, and Metabolites Reveals Bone Defect-Specific Molecular Profiles. PLoS One 11, e0159580 (2016).

[50]. Hines, K. M., et al. (2013). "Biomolecular signatures of diabetic wound healing by structural mass spectrometry." Analytical Chemistry 85(7): 3651-3659.

What is claimed is:

1. A system for microdialysis imaging and regional fluidic delivery and control for dialyzing/retrodialyzing/culturing/controlling/analyzing the living bio-object, wherein the living bio-object comprises cells, tissues, slices, or an organ of a living subject, comprising:
   a microdialysis imager comprising a imaging head having N pixels aligned in a pixel array for monitoring a state of a living bio-object that is in fluidic communication with the pixel array, N being a positive integer greater than one; and
   a fluidic module coupled to the microdialysis imager for delivering a fluidic substance to and collecting effluent from the living bio-object, the fluidic module comprising a fluidic network having a plurality of valves, a plurality of fluidic channels in fluidic communication with the plurality of valves and one or more pumps coupled to corresponding fluidic channels, and a microcontroller coupled to the fluidic network for individually controlling the plurality of valves and the one or more pumps of the fluidic network as so to operably and selectively deliver the fluidic substance to and continuously collect the effluent from the living bio-object responsive to the delivered fluidic substance via each pixel of the pixel array in real time.

2. The system of claim 1, wherein each pixel comprises a delivery channel and a collection channel in fluidic communication with each other and the N pixels are aligned such that the pixel array has a first end and an opposite, second end, and wherein the imaging head further comprises a semipermeable membrane disposed on the first end of the pixel array.

3. The system of claim 2, wherein each of the delivery and collection channels of each pixel is in a tube whose end area defines a pixel area.

4. The system of claim 3, wherein the delivery channel and the collection channel of each pixel is separated by a wall that defines a gap at the first end of each pixel of the pixel array so that the delivery channel and the collection channel of each pixel are in fluidic communication with each other via the gap.

5. The system of claim 3, wherein the imaging head is formed as a ribbon whose end area defines an area of the pixel array.

6. The system of claim 2, wherein the microdialysis imager further comprises
   a microdialysis membrane disposed on the semipermeable membrane of the imaging head for placing the living bio-object thereon; and
   a layer of cell culture or perfusion media disposed on the microdialysis membrane.

7. The system of claim 6, wherein the microdialysis imager is in fluidic communication with the plurality of fluidic channels via the second end of the pixel array.

8. The system of claim 7, wherein the delivery of the fluidic substance to and the collection of the effluent from the living bio-object in each pixel of the pixel array are via the second end of the pixel array.

9. The system of claim 8, wherein the first and second ends of the pixel array are top and bottom ends of the pixel array, respectively, so that the microdialysis imager is in an inverted geometry.

10. The system of claim 6, wherein the microdialysis imager further comprises a microelectrode array (MEA) superimposed on the semipermeable membrane, wherein the MEA is corresponding to the pixel array with each pair of electrodes coupled to a respective pixel for detecting electrical activity of the living bio-object in an immediate vicinity of the respective pixel.

11. The system of claim 10, wherein the MEA is provided as a substrate disposed between the semipermeable/microdialysis membrane and the bio-object, wherein the substrate has through holes, each through hole being corresponding to a respective underlying pixel to allow fluidic communication with the respective underlying pixel, and wherein the electrodes are connected to detection electronics by thin-film leads.

12. The system of claim 2, wherein the semipermeable membrane is made of polyarylonitrile, AN69, cuprophane, polycarbonate, polyamide, polysufone, polyarylethersulfone, or a combination thereof.

13. The system of claim 1, wherein each valve is a rotary planar valve (RPV), and wherein each pump is a rotary planar peristaltic micropump (RPPM).

14. The system of claim 1, wherein the fluidic module comprises a delivery control unit disposed on one side of the microdialysis imager, and a collection control unit disposed on the other side of the microdialysis imager, wherein the delivery control unit, the microdialysis imager and the collection control unit are in fluidic communication with each other, so that input and output of each pixel of the pixel array are operably controllable by the delivery control unit and/or the collection control unit.

15. The system of claim 1, wherein the fluidic module comprises a delivery control unit disposed on one side of the microdialysis imager, and a collection control unit disposed on the same side of the microdialysis imager, wherein the delivery control unit, the microdialysis imager and the collection control unit are in fluidic communication with each other, so that input and output of each pixel of the pixel array are operably controllable by the delivery control unit and/or the collection control unit.

16. The system of claim 14, wherein
the delivery control unit comprises at least one multi-channel input selector valve coupled to a plurality of input ports that operably provides a plurality of fluids, at least one input pump coupled to the at least one multi-channel input selector valve, and at least one multi-channel input director valve coupled to the at least one input pump;
the collection control unit comprises at least one multi-channel output collector valve, at least one output pump coupled to the at least one multi-channel output collector valve and at least one multi-channel output director valve; and
the microdialysis imager is coupled between the at least one multi-channel input director valve of the delivery control unit and the at least one multi-channel output collector valve of the collection control unit.

17. The system of claim 16, further comprising an analyzer unit coupled to the at least one multi-channel output director valve of the collection control unit.

18. The system of claim 17, wherein the analyzer unit comprises a at least one of a fluorimeter, an electrochemical analyzer, a capillary electrophoresis detector, a liquid chromatography detector, a radiation detector, an impedance/conductance analyzer, a mass spectrometer, chemical detectors, or combinations thereof.

19. The system of claim 1, wherein the fluidic module is configured such that the fluidic substance delivered to the living bio-object is identical in each pixel of the pixel array, or different in different pixels of the pixel array.

20. The system of claim 19, wherein the fluidic substance contains one or more fluids with a concentration of each fluid controllable in real time.

21. The system of claim 19, wherein the fluidic substance has a one-dimensional or two-dimensional concentration gradient distribution across the pixel array.

22. The system of claim 19, wherein the fluidic substance contains perfusate or drugs, and the effluent contains dialysate or waste from the living bio-object.

23. A method for microdialysis imaging and regional fluidic delivery and control for dialyzing/retrodialyzing/culturing/controlling/analyzing a living bio-object, wherein the living bio-object comprises cells, tissues, or an organ of a living subject, comprising:
providing a microdialysis imager and a fluidic network, wherein the microdialysis imager comprises a imaging head having N pixels aligned in a pixel array for monitoring a state of the living bio-object that is in fluidic communication with the pixel array, N being a positive integer greater than one, and wherein the fluidic network is coupled to the microdialysis imager and a plurality of fluids and comprises a plurality of valves, a plurality of fluidic channels in fluidic communication with the plurality of valves, and one or more pumps coupled to corresponding fluidic channels; and
individually controlling the plurality of valves and the one or more pumps of the fluidic network to operably and selectively deliver a fluidic substance to and continuously collect the effluent from the living bio-object responsive to the delivered fluidic substance via each pixel of the pixel array in real time, wherein the fluidic substance contains one or more of the plurality of fluids.

24. The method of claim 23, wherein the controlling step comprises controlling the fluidic substance delivered to the living bio-object to be identical in each pixel of the pixel array, or to be different in different pixels of the pixel array.

25. The method of claim 24, wherein the controlling step comprises controlling the fluidic substance to have a concentration of each fluid being constant or varying with time.

26. The method of claim 25, wherein the controlling step comprises controlling the fluidic substance to have a one-dimensional or two-dimensional concentration gradient distribution across the pixel array.

27. The method of claim 24, wherein the fluidic substance contains perfusate or drugs, and the effluent contains dialysate or waste from the living bio-object.

28. The method of claim 23, wherein the controlling step comprises parallel pixel delivery of the fluidic substance, parallel pixel collection of the effluent, and serial pixel readout of the effluent.

29. The method of claim 28, wherein the controlling step comprises M clock steps, M being a positive integer equal to or less than N, wherein in each clock step, a single aliquot of the fluidic substance is delivered sequentially to each pixel in N pixel steps, such that at any time, each pixel contains a different number of aliquots so that only one pixel is ready for analysis in each clock step, and then the aliquots in that pixel are collected for analysis, and the delivery and collection process in each clock step is repeated for all M clock steps, so that after the Nth aliquot is delivered to a pixel and allowed to dialyze the living bio-object, the N aliquots are then collected and transferred to an analyzer, and a single, fresh, aliquot is left in that pixel to start a new full cycle.

30. The method of claim 29, wherein during N full cycles, the effluent of each pixel is transferred to the analyzer as a single bolus containing N aliquots.

31. The method of claim 29, further comprising providing demarcation between a bolus of the effluent that is delivered to the analyzer from different pixels.

32. The method of claim 31, wherein the step of providing demarcation comprises injecting a bubble of air between boluses of the effluent from different pixels, so that the end of one bolus of the effluent and the beginning of another bolus of the effluent are detectable by a bubble detector.

33. The method of claim 23, further comprising analyzing the effluent so as to monitor the state of the living bio-object.

34. The method of claim 23, wherein each pixel comprises a delivery channel and a collection channel in fluidic communication with each other, wherein each of the delivery and collection channels of each pixel is in a tube whose end area defines a pixel area.

35. The method of claim 23, wherein the valves in the system can be back-flushed to avoid cross-contamination between pixels that have different compositions of the dialysate that is delivered to sequentially filled pixels.

* * * * *